US006417358B1

(12) United States Patent
Tinkl et al.

(10) Patent No.: US 6,417,358 B1
(45) Date of Patent: Jul. 9, 2002

(54) PROCESS FOR THE PREPARATION OF 3-ARYL-BENZOFURANONES

(75) Inventors: Michael Tinkl, Grenzach-Wyhlen (DE); Samuel Evans; Peter Nesvadba, both of Marly (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/720,442

(22) PCT Filed: Jun. 15, 1999

(86) PCT No.: PCT/EP99/04117

§ 371 (c)(1),
(2), (4) Date: Dec. 22, 2000

(87) PCT Pub. No.: WO99/67232

PCT Pub. Date: Dec. 29, 1999

(30) Foreign Application Priority Data

Jun. 25, 1998 (CH) .............................................. 1355/98

(51) Int. Cl.[7] .................... C07D 221/12; C07D 239/72; C07D 307/91; C07D 311/82; C07D 475/00
(52) U.S. Cl. ........................ 544/253; 544/257; 546/102; 546/108; 546/152; 546/278.4; 548/284.1; 548/463; 548/525; 549/60; 549/223; 549/299; 549/304
(58) Field of Search ................................ 544/253, 257; 546/102, 108, 152, 278.4; 548/284.1, 463, 525; 549/60, 223, 299, 304

(56) References Cited

U.S. PATENT DOCUMENTS

| 4,006,252 A | 2/1977 | Lerner ......................... 424/331 |
| 4,325,863 A | 4/1982 | Hinsken et al. ............. 624/111 |
| 5,607,624 A | 3/1997 | Nesvadba et al. .......... 252/589 |

FOREIGN PATENT DOCUMENTS

| EP | 0176370 | 4/1986 |
| EP | 0648765 | 4/1995 |
| WO | 80/01566 | 8/1980 |

OTHER PUBLICATIONS

L. Jurd, J. Heterocyclic Chem., vol. 25, (1988), pp. 89–96.
C. Wörner et al, Angew. Chem. Int. Ed. Engl., vol. 32, No. 9, (1993), pp. 1306–1308.
Chem. Abstr. 100:149865 for M. Benson et al., Org. Magn. Reson. vol. 22, No. 2, (1984), pp. 86–89.
Chem. Abstr. 76:140285 for C. Brieskorn et al., Arch. Pharm. (Weinheim), (1972), vol. 305, No. 2, pp. 141–148.
Patent Abstracts of Japan Publication No. 05005913, (1993).
R. F. Heldeweg et al., J. Am. Chem. Soc. vol. 98, No. 19, (1976), pp. 6040–6042.

*Primary Examiner*—T. A. Solola
(74) *Attorney, Agent, or Firm*—Tyler A. Stevenson

(57) ABSTRACT

Process for the preparation of compounds of formula (I), wherein the general symbols are as defined in claim 1, which process comprises reacting a compound of formula (V), wherein the general symbols are as defined in claim 1, with carbon monoxide in the presence of a catalyst.

17 Claims, No Drawings

PROCESS FOR THE PREPARATION OF 3-ARYL-BENZOFURANONES

This Application is a 371 PCT/EP99,04417 filed Jun. 15, 1999.

The present invention relates to a novel process for the preparation of 3-aryl-benzofuran-ones, which are suitable for stabilising organic materials against oxidative, thermal or light-induced degradation.

The best processes hitherto for the preparation of 3-aryl-benzofuranones are described, for example, in U.S. Pat. No. 4,325,863 and U.S. Pat. No. 5,607,624.

The process disclosed in U.S. Pat. No. 4,325,863 (Example 1, column 8, lines 35–45) for the preparation of 3-phenyl-3H-benzofuran-2-ones, for example 5,7-di-tert-butyl-3-phenyl-3H-benzofuran-2-one of formula C, comprises reacting the 2,4-di-tert-butylphenol of formula A with the mandelic acid of formula B, with removal of water.

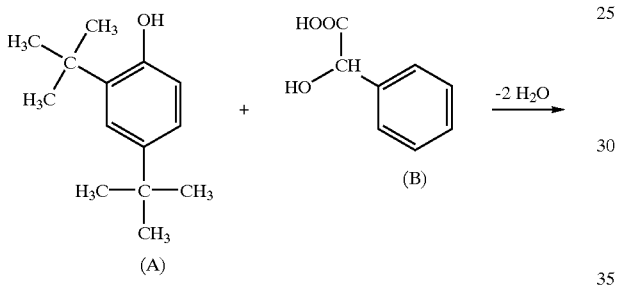

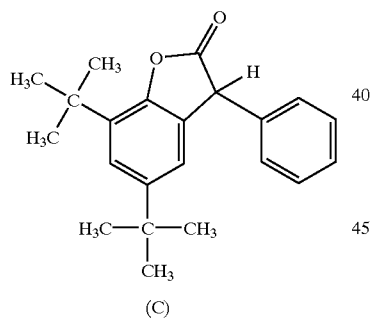

A disadvantage of that process is that it requires the use of mandelic acids substituted on the phenyl ring or heterocyclic mandelic acids. Not very many of those mandelic acids are known from the literature, however, and the known synthesis procedures for the preparation thereof are relatively complicated.

The process disclosed in U.S. Pat. No. 5,607,624 (Example 1, column 24) for the preparation of 3-phenyl-3H-benzofuran-2-ones substituted on the 3-phenyl ring, for example 5,7-di-tert-butyl-3-(2,5-dimethyl-phenyl)-3H-benzofuran-2-one of formula F, comprises reacting the 5,7-di-tert-butyl-3-hydroxy-3H-benzofuran-2-one of formula D with p-xylene of formula E, with removal of water.

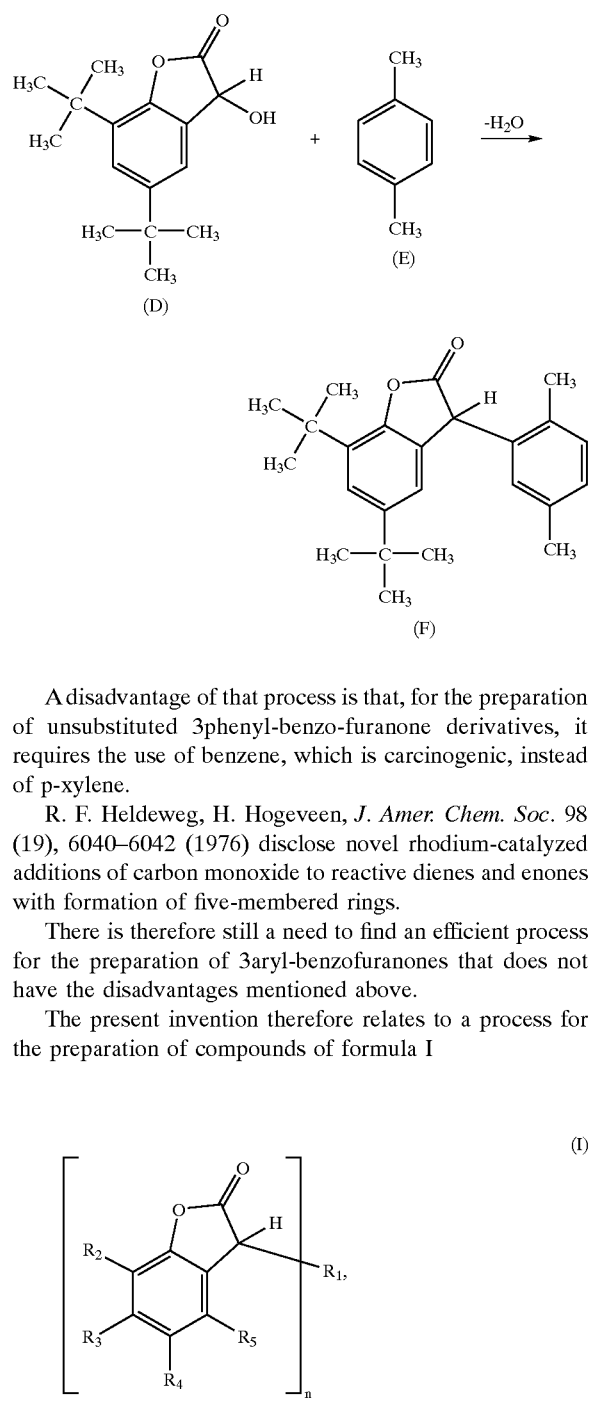

A disadvantage of that process is that, for the preparation of unsubstituted 3phenyl-benzo-furanone derivatives, it requires the use of benzene, which is carcinogenic, instead of p-xylene.

R. F. Heldeweg, H. Hogeveen, *J. Amer. Chem. Soc.* 98 (19), 6040–6042 (1976) disclose novel rhodium-catalyzed additions of carbon monoxide to reactive dienes and enones with formation of five-membered rings.

There is therefore still a need to find an efficient process for the preparation of 3aryl-benzofuranones that does not have the disadvantages mentioned above.

The present invention therefore relates to a process for the preparation of compounds of formula I wherein, when n is 1, $R^1$ is naphthyl, phenanthryl, anthryl, 5,6,7,8-tetrahydro-2-naphthyl, thienyl, benzo[b]thienyl, naphtho[2,3-b] thienyl, thianthrenyl, furyl, benzofuryl, isobenzofuryl, dibenzofuryl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by fluorine, hydroxy, $C_1$–$C_{18}$alkyl, $C_1$–$C_{18}$alkoxy, $C_1$–$C_{18}$alkylthio, di-($C_1$–$C_4$alkyl)amino, phenyl, benzyl, benzoyl or by benzoyloxy or $R_1$ is a radical of formula II or III

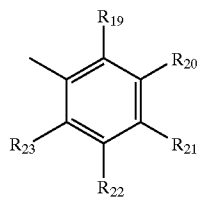
(II)

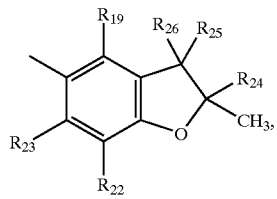
(III)

when n is 2, $R_1$ is phenylene or naphthylene each unsubstituted or substituted by $C_1$–$C_4$alkyl or by fluorine; or is —$R_6$—X—$R_7$—, $R_2$, $R_3$, $R_4$ and $R_5$ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —$(CH_2)_p$—$COR_9$ or —$(CH_2)_q$OH or, when $R_3$ and $R_5$ are hydrogen, $R_4$ is additionally a radical of formula IV

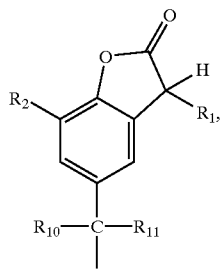
(IV)

wherein $R_1$ is as defined above for the case where n=1, $R_6$ and $R_7$ are each independently of the other phenylene or naphthylene each unsubstituted or substituted by $C_1$–$C_4$alkyl, $R_8$ is $C_1$–$C_8$alkyl, $R_9$ is hydroxy, $$\left[-O-\frac{1}{r}M^{r+}\right],$$

$C_1$–$C_{18}$alkoxy or

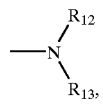

$R_{10}$ and $R_{11}$ are each independently of the other hydrogen, $CF_3$, $C_1$–$C_{12}$alkyl or phenyl, or $R_{10}$ and $R_{11}$, together with the carbon atom to which they are bonded, form a $C_5$–$C_8$cycloalkylidene ring unsubstituted or substituted by from 1 to 3 $C_1$–$C_4$alkyl groups;

$R_{12}$ and $R_{13}$ are each independently of the other hydrogen or $C_1$–$C_{18}$alkyl, $R_{14}$ is hydrogen or $C_1$–$C_{18}$alkyl, $R_{19}$, $R_{20}$, $R_{21}$, $R_{22}$ and $R_{23}$ are each independently of the others hydrogen, fluorine, hydroxy, $C_1$–$C_{25}$alkyl; $C_2$–$C_{25}$alkyl interrupted by oxygen, sulfur or by

$C_1$–$C_{25}$alkoxy; $C_2$–$C_{25}$alkoxy interrupted by oxygen, sulfur or by

$C_1$–$C_{25}$alkylthio, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; di($C_1$–$C_4$alkyl)amino, $C_1$–$C_{25}$-alkanoyl; $C_3$–$C_{25}$alkanoyl interrupted by oxygen, sulfur or by

$C_1$–$C_{25}$alkanoyloxy; $C_3$–$C_{25}$alkanoyloxy interrupted by oxygen, sulfur or by

$C_1$–$C_{25}$alkanoylamino, $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

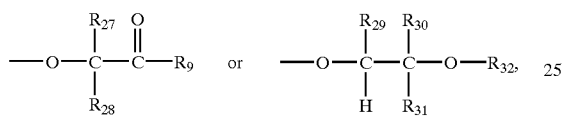

$R_{24}$ is hydrogen, $C_1$–$C_4$alkyl, or unsubstituted or $C_1$–$C_4$alkyl-substituted phenyl, $R_{25}$ and $R_{26}$ are hydrogen, $C_1$–$C_4$alkyl or phenyl, with the proviso that at least one of the radicals $R_{25}$ and $R_{26}$ is hydrogen, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{25}$alkyl; $C_2$–$C_{25}$alkyl interrupted by oxygen, sulfur or by

$C_7$–$C_9$phenylalkyl unsubstituted or substituted on the phenyl radical by from 1 to 3 $C_1$–$C_4$alkyl groups; or $C_7$–$C_{25}$phenylalkyl interrupted by oxygen, sulfur or by

and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{25}$alkanoyl; $C_3$–$C_{25}$alkanoyl interrupted by oxygen, sulfur or by

$C_2$–$C_{25}$alkanoyl substituted by a di($C_1$–$C_6$alkyl) phosphonate group; $C_6$–$C_9$cyclo-alkylcarbonyl, thenoyl, furoyl, benzoyl or $C_1$–$C_{12}$alkyl-substituted benzoyl;

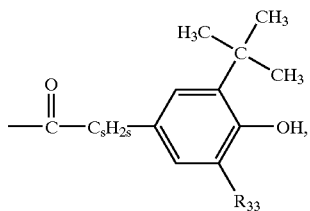

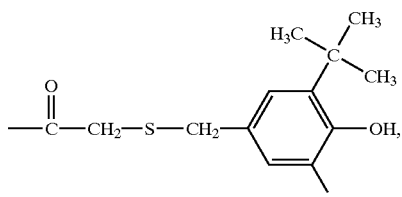

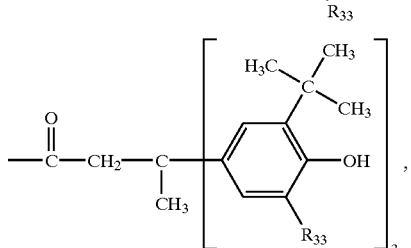

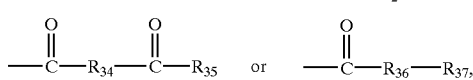

$R_{33}$ is hydrogen or $C_1$–$C_8$alkyl, $R_{34}$ is a direct bond, $C_1$–$C_{18}$alkylene; $C_2$–$C_{18}$alkylene interrupted by oxygen, sulfur or by

$C_2$–$C_{20}$alkylidene, $C_7$–$C_{20}$phenylalkylidene, $C_5$–$C_8$cycloalkylene, $C_7$–$C_8$bicyclo-alkylene, unsubstituted or $C_1$–$C_4$alkyl-substituted phenylene,

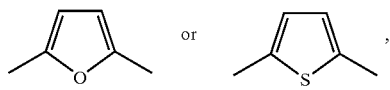

$R_{35}$ is hydroxy,

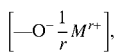

$C_1$–$C_{18}$alkoxy or

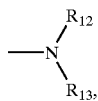

$R_{36}$ is oxygen, —NH— or

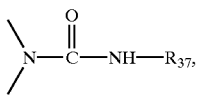

$R_{37}$ is $C_1$–$C_{18}$alkyl or phenyl,
M is an r-valent metal cation,
X is a direct bond, oxygen, sulfur or —$NR_{14}$—,
n is 1 or 2,
p is 0, 1 or 2,
q is 1, 2, 3, 4, 5 or 6,
r is 1, 2 or 3, and
s is 0, 1 or 2,
which process comprises reacting a compound of formula V

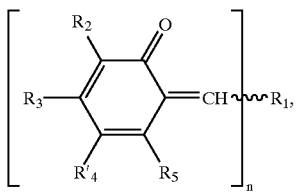

(V)

wherein
$R_1$ and n are as defined above,
$R_2$, $R_3$, $R'_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$-cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R'_4$ or the radicals $R'_4$ and $R_5$, together with the carbon atoms to which they are bonded, form a benzo ring, $R'_4$ is additionally —$(CH_2)_p$—$COR_9$ or —$(CH_2)_q$OH or, when $R_3$ and $R_5$ are hydrogen,
$R'_4$ is additionally a radical of formula VI

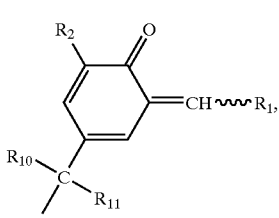

(VI)

wherein $R_1$ is as defined above for the case where n=1, with carbon monoxide in the presence of a catalyst.

Alkanoyl having up to 25 carbon atoms is a branched or unbranched radical, for example formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, icosanoyl or docosanoyl. Alkanoyl has preferably from 2 to 18, especially from 2 to 12, e.g. from 2 to 6, carbon atoms. Special preference is given to acetyl.

$C_2$–$C_{25}$Alkanoyl substituted by a di($C_1$–$C_6$alkyl) phosphonate group is, for example, $(CH_3CH_2O)_2POCH_2CO$—, $(CH_3O)_2POCH_2CO$—, $(CH_3CH_2CH_2CH_2O)_2POCH_2CO$—, $(CH_3CH_2O)_2POCH_2CH_2CO$—, $(CH_3O)_2POCH_2CH_2CO$—, $(CH_3CH_2CH_2O)_2POCH_2CH_2CO$—, $(CH_3CH_2O)_2PO(CH_2)_4CO$—, $(CH_3CH_2O)_2PO(CH_2)_8CO$— or $(CH_3CH_2O)_2PO(CH_2)_{17}CO$—.

Alkanoyloxy having up to 25 carbon atoms is a branched or unbranched radical, for example formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, icosanoyloxy or docosanoyloxy. Preference is given to alkanoyloxy having from 2 to 18, especially from 2 to 12, e.g. from 2 to 6, carbon atoms. Special preference is given to acetoxy.

$C_3$–$C_{25}$Alkenoyloxy interrupted by oxygen, sulfur or by

is, for example, $CH_3OCH_2CH_2CH=CHCOO$— or $CH_3OCH_2CH_2OCH=CHCOO$—.

$C_3$–$C_{25}$Alkanoyl interrupted by oxygen, sulfur or by

is, for example, $CH_3$—O—$CH_2CO$—, $CH_3$—S—$CH_2CO$—, $CH_3$—N($CH_3$)—$CH_2CO$—, $CH_3$—O—$CH_2CH_2$—O—$CH_2CO$—, $CH_3$—(O—$CH_2CH_2$—)$_2$O—$CH_2CO$—, $CH_3$—(O—$CH_2CH_2$—)$_3$—O—$CH_2CO$— or $CH_3$—(O—$CH_2CH_2$—)$_4$—$CH_2CO$—.

$C_3$–$C_{25}$Alkanoyloxy interrupted by oxygen, sulfur or by

is, for example, $CH_3$—O—$CH_2COO$—, $CH_3$—S—$CH_2COO$—, $CH_3$—N($CH_3$)—$CH_2COO$—, $CH_3$—O—$CH_2CH_2$—O—$CH_2COO$—, $CH_3$—(O—$CH_2CH_2$—)$_2$O—$CH_2COO$—, $CH_3$—(O—$CH_2CH_2$—)$_3$O—$CH_2COO$— or $CH_3$—(O—$CH_2CH_2$—)$_4$O—$CH_2COO$—.

$C_6$–$C_9$Cycloalkylcarbonyl is, for example, cyclopentylcarbonyl, cyclohexylcarbonyl, cycloheptylcarbonyl or cyclooctylcarbonyl. Preference is given to cyclohexylcarbonyl.

$C_6$–$C_9$Cycloalkylcarbonyloxy is, for example, cyclopentylcarbonyloxy, cyclohexylcarbonyloxy, cycloheptylcarbonyloxy or cyclooctylcarbonyloxy. Preference is given to cyclohexylcarbonyloxy.

$C_1$–$C_{12}$Alkyl-substituted benzoyl, which carries preferably from 1 to 3, especially 1 or 2, alkyl groups, is, for example, o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$-alkyl, especially $C_1$-$C_4$alkyl.

$C_1$–$C_{12}$Alkyl-substituted benzoyloxy, which carries preferably from 1 to 3, especially 1 or 2, alkyl groups, is, for example, o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy. Preferred substituents are $C_1$–$C_8$alkyl, especially $C_1$–$C_4$alkyl.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl. One of the preferred definitions for $R_2$ and $R_4$ is, for example, $C_1$–$C_{18}$alkyl. An especially preferred definition for $R_4$ is $C_1$–$C_4$alkyl.

$C_2$–$C_{25}$Alkyl interrupted by oxygen, sulfur or by

is, for example, $CH_3$—O—$CH_2$—, $CH_3$—S—$CH_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

$C_7$–$C_9$Phenylalkyl is, for example, benzyl, α-methylbenzyl, α,α-dimethylbenzyl or 2-phenylethyl. Preference is given to benzyl and α,α-dimethylbenzyl.

$C_7$–$C_9$Phenylalkyl unsubstituted or substituted on the phenyl radical by from 1 to 3 $C_1$–$C_4$alkyl groups is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tertbutylbenzyl. Preference is given to benzyl.

$C_7$–$C_{25}$Phenylalkyl interrupted by oxygen, sulfur or by

and unsubstituted or substituted on the phenyl radical by from 1 to 3 $C_1$–$C_4$alkyl groups is a branched or unbranched radical, for example phenoxymethyl, 2-methyl-phenoxymethyl, 3-methyl-phenoxymethyl, 4-methyl-phenoxymethyl, 2,4-dimethyl-phenoxymethyl, 2,3-dimethyl-phenoxymethyl, phenyl-thiomethyl, N-methyl-N-phenyl-aminomethyl, N-ethyl-N-phenyl-aminomethyl, 4-tert-butyl-phenoxymethyl, 4-tert-butyl-phenoxyethoxymethyl, 2,4-di-tert-butyl-phenoxymethyl, 2,4-di-tert-butyl-phenoxyethoxymethyl, phenoxyethoxyethoxyethoxymethyl, benzyloxymethyl, benzyloxyethoxymethyl, N-benzyl-N-ethyl-aminomethyl or N-benzyl-N-isopropyl-aminomethyl.

$C_7$–$C_9$Phenylalkoxy is, for example, benzyloxy, α-methylbenzyloxy, α,α-dimethylbenzyloxy or 2-phenylethoxy. Preference is given to benzyloxy.

$C_1$–$C_4$Alkyl-substituted phenyl, which contains preferably from 1 to 3, especially 1 or 2, alkyl groups, is, for example, o-, m- or p-methylphenyl, 2,3-dimethyiphenyi, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_1$–$C_4$Alkyl-substituted phenoxy, which contains preferably from 1 to 3, especially 1 or 2, alkyl groups, is, for example, o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

Unsubstituted or $C_1$–$C_4$alkyl-substituted $C_5$-Cacycloalkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Preference is given to cyclohexyl and tert-butylcyclohexyl.

Unsubstituted or $C_1$–$C_4$alkyl-substituted $C_5$–$C_8$cycloalkoxy is, for example, cyclopentyloxy, methylcyclopentyloxy, dimethylcyclopentyloxy, cyclohexyloxy, methylcyclohexyloxy, dimethylcyclohexyloxy, trimethylcyclohexyloxy, tert-butylcyclohexyloxy, cycloheptyloxy or cyclooctyloxy. Preference is given to cyclohexyloxy and tert-butylcyclohexyloxy.

Alkoxy having up to 25 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy. Preference is given to alkoxy having from 1 to 12, especially from 1 to 8, e.g. from 1 to 6, carbon atoms.

$C_2$–$C_{25}$Alkoxy interrupted by oxygen, sulfur or by

is for example, $CH_3$—O—$CH_2CH_2O$—, $CH_3$—S—$CH_2CH_2O$—, $CH_3$—N($CH_3$)—$CH_2CH_2O$—, $CH_3$—O—$CH_2CH_2$—O—$CH_2CH_2O$—, $CH_3$—(O—$CH_2CH_2$—)$_2$O—$CH_2CH_2O$—, $CH_3$—(O—$CH_2CH_2$—)$_3$O—$CH_2CH_2O$— or $CH_3$—(O—$CH_2CH_2$—)$_4$O—$CH_2CH_2O$—.

Alkylthio having up to 25 carbon atoms is a branched or unbranched radical, for example methylthio, ethylthio, propylthio, isopropylthio, n-butylthio, isobutylthio, pentylthio, isopentylthio, hexylthio, heptyithio, octylthio, decylthio, tetradecylthio, hexadecylthio or octadecylthio. Preference is given to alkyithio having from 1 to 12, especially from 1 to 8, e.g. from 1 to 6, carbon atoms.

Alkylamino having up to 4 carbon atoms is a branched or unbranched radical, for example methylamino, ethylamino, propylamino, isopropylamino, n-butylamino, isobutylamino or tert-butylamino.

Di($C_1$–$C_4$alkyl)amino means also that the two radicals are each independently of the other branched or unbranched, for example, dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylamino, diisopropylamino, isopropyl-n-butylamino, isopropylisobutylamino, di-n-butylamino or di-isobutylamino.

Alkanoylamino having up to 25 carbon atoms is a branched or unbranched radical, for example formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, icosanoylamino or docosanoylamino. Preference is given to alkanoylamino having from 2 to 18, especially from 2 to 12, e.g. from 2 to 6, carbon atoms.

$C_1$–$C_{18}$Alkylene is a branched or unbranched radical, for example methylene, ethylene, propylene, trimethylene, tetramethylene, pentamethylene, hexamethylene, heptamethylene, octamethylene, decamethylene, dodecamethylene or octadecamethylene. Preference is given to $C_1$–$C_{12}$alkylene, especially $C_1$–$C_8$alkylene. An especially preferred definition for $R_{56}$ is $C_2$–$C_8$alkylene, especially $C_4$–$C_8$alkylene, for example tetramethylene or pentamethylene.

$C_2$–$C_{18}$Alkylene interrupted by oxygen, sulfur or by

is, for example, —$CH_2$—O—$CH_2$—, —$CH_2$—S—$CH_2$—, —$CH_2$—N($CH_3$)—$CH_2$—, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)$_3$O—$CH_2$—, —$CH_2$—(O—$CH_2CH_2$—)$_4$O—$CH_2$— or —$CH_2CH_2$—S—$CH_2CH_2$—.

Alkylidene having from 2 to 20 carbon atoms is, for example, ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. Preference is given to $C_2$–$C_8$alkylidene.

Phenylalkylidene having from 7 to 20 carbon atoms is, for example, benzylidene, 2-phenylethylidene or 1-phenyl-2-hexylidene. Preference is given to $C_7$–$C_9$phenylalkylidene.

$C_5$–$C_8$Cycloalkylene is a saturated hydrocarbon group having two free valences and at least one ring unit and is, for example, cyclopentylene, cyclohexylene, cycloheptylene or cyclooctylene. Preference is given to cyclohexylene.

$C_7$–$C_8$Bicycloalkylene is, for example, bicycloheptylene or bicyclooctylene.

Phenytene or naphthylene each unsubstituted or substituted by $C_1$–$C_4$alkyl is, for example, 1,2-, 1,3- or 1,4-phenylene or 1,2-, 1,3-, 1,4-, 1,6-, 1,7-, 2,6- or 2,7-naphthylen is given to 1,4-phenylene.

A $C_5$–$C_8$cycloalkylidene ring substituted by $C_1$–$C_4$alkyl, which contains preferably from 1 to 3, especially 1 or 2, branched or unbranched alkyl group radicals, is, for example, cyclopentylidene, methylcyclopentylidene, dimethylcyciopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene and tert-butylcyclohexylidene.

A mono-, di- or tri-valent metal cation is preferably an alkali metal cation, alkaline earth metal cation or aluminium cation, for example $Na^+$, $K^+$, $Mg^{++}$, $Ca^{++}$ or $Al^{+++}$.

Dendrimeric, oligomeric or polymeric $C_4$–$C_{100}$hydrocarbon radicals are, for example, those such as are disclosed by R. Mülhaupt et al. in Angew. Chem., Int. Ed. 32 (9), 1306 (1993).

Of interest is a process for the preparation of compounds of formula I wherein, when n is 2, $R_1$ is phenylene or —$R_6$—X—$R_7$—, $R_6$ and $R_7$ are phenylene, —X is oxygen or —$NR_{14}$—, and $R_{14}$ is $C_1$–$C_4$alkyl.

Likewise of interest is a process for the preparation of compounds of formula I wherein $R_{19}$, $R_{20}$, $R_{21}$, $R_{22}$ and $R_{23}$ are each independently of the others hydrogen, fluorine, hydroxy, $C_1$–$C_{18}$alkyl; $C_2$–$C_{18}$alkyl interrupted by oxygen or by sulfur; $C_1$–$C_{18}$alkoxy; $C_2$–$C_{18}$alkoxy interrupted by oxygen or by sulfur; $C_1$–$C_{18}$alkylthio, $C_7$–$C_9$phenylalkyl, $C_7$–$C_9$phenylalkoxy, unsubstituted or $C_1$–$C_4$alkyl-substituted phenyl; phenoxy, cyclohexyl, $C_5$–$C_8$cycloalkoxy, di($C_1$–$C_4$-alkyl)amino, $C_1$–$C_{12}$alkanoyl; $C_3$–$C_{12}$alkanoyl interrupted by oxygen or by sulfur; $C_1$–$C_{12}$-alkanoyloxy; $C_3$–$C_{12}$alkanoyloxy interrupted by oxygen or by sulfur; $C_1$–$C_{12}$alkanoylamino, cyclohexylcarbonyl, cyclohexylcarbonyloxy, benzoyl or $C_1$–$C_4$alkyl-substituted benzoyl; benzoyloxy or $C_1$–$C_4$alkyl-substituted benzoyloxy;

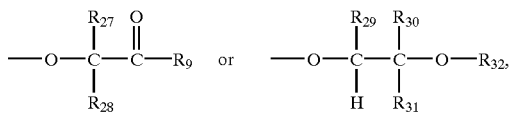

$R_{24}$ is hydrogen or $C_1$–$C_4$alkyl, $R_{25}$ and $R_{26}$ are hydrogen or $C_1$–$C_4$alkyl, with the proviso that at least one of the radicals $R_{25}$ and $R_{26}$ is hydrogen, $R_{27}$ and $R_{28}$ are each independently of the other hydrogen or $C_1$–$C_4$alkyl, $R_{29}$ is hydrogen, $R_{30}$ is hydrogen, phenyl, $C_1$–$C_{18}$alkyl; $C_2$–$C_{18}$alkyl interrupted by oxygen or by sulfur; $C_7$–$C_9$-phenylalkyl; or $C_7$–$C_{18}$phenylalkyl interrupted by oxygen or by sulfur and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{18}$alkanoyl; $C_3$–$C_{12}$alkanoyl interrupted by oxygen or by sulfur; $C_2$–$C_{12}$-alkanoyl substituted by a di($C_1$–$C_6$alkyl) phosphonate group; $C_6$–$C_9$cycloalkylcarbonyl, benzoyl,

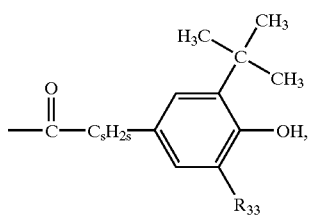

-continued

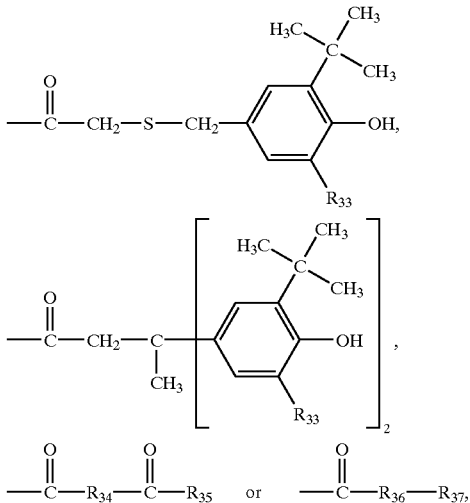

$R_{33}$ is hydrogen or $C_1$–$C_4$alkyl,
$R_{34}$ is $C_1$–$C_{12}$alkylene, $C_2$–$C_8$alkylidene, $C_7$–$C_{12}$phenylalkylidene, $C_5$–$C_8$cycloalkylene or phenylene,
$R_{35}$ is hydroxy,

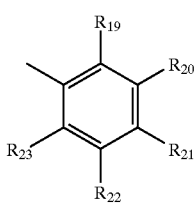

or $C_1$–$C_{18}$alkoxy,
$R_{36}$ is oxygen or —NH—,
$R_{37}$ is $C_1$–$C_8$alkyl or phenyl, and
s is 1 or 2.

Of special interest is a process for the preparation of compounds of formula I wherein, when n is 1,
$R_1$ is phenanthryl, thienyl, dibenzofuryl, unsubstituted or $C_1$–$C_4$alkyl-substituted carbazolyl; or fluorenyl, or $R_1$ is a radical of formula II (II)

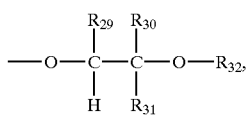

wherein
$R_{19}$, $R_{20}$, $R_{21}$, $R_{22}$ and $R_{23}$ are each independently of the others hydrogen, fluorine, hydroxy, $C_1$–$C_{18}$alkyl, $C_1$–$C_{18}$alkoxy, $C_1$–$C_{18}$alkylthio, phenyl, benzoyl, benzoyloxy or

—O—C(R_{29})(R_{30})—C(H)(R_{31})—O—R_{32}, $R_{29}$ is hydrogen,
$R_{30}$ is hydrogen, phenyl or $C_1$–$C_{18}$alkyl,
$R_{31}$ is hydrogen or $C_1$–$C_4$alkyl, and
$R_{32}$ is hydrogen, $C_1$–$C_{12}$alkanoyl or benzoyl.

Likewise of special interest is a process for the preparation of compounds of formula I wherein $R_{19}$ is hydrogen or $C_1$–$C_4$alkyl,
$R_{20}$ is hydrogen or $C_1$–$C_4$alkyl,
$R_{21}$ is hydrogen, fluorine, hydroxy, $C_1$–$C_{12}$alkyl, $C_1$–$C_4$alkoxy, $C_1$–$C_4$alkylthio, phenyl or —O—CH$_2$—CH$_2$—O—$R_{32}$,
$R_{22}$ is hydrogen or $C_1$–$C_4$alkyl,
$R_{23}$ is hydrogen or $C_1$–$C_4$alkyl, and
$R_{32}$ is $C_1$–$C_4$alkanoyl.

Of special interest is, more especially, a process for the preparation of compounds of formula I wherein
$R_2$, $R_3$, $R_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; $C_1$–$C_{12}$alkoxy, $C_1$–$C_{12}$alkylthio, $C_1$–$C_4$alkylamino, di-($C_1$–$C_4$alkyl)amino, $C_1$–$C_{18}$alkanoyloxy, $C_1$–$C_{18}$alkanoylamino; $C_3$–$C_{18}$alkanoyloxy interrupted by oxygen, sulfur or by

$C_6$–$C_9$cycloalkylcarbonyloxy, benzoyloxy or $C_1$–$C_8$alkyl-substituted benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —(CH$_2$)$_p$—COR$_9$ or —(CH$_2$)$_q$OH or, when $R_3$ and $R_5$ are hydrogen, $R_4$ is additionally a radical of formula IV (IV)

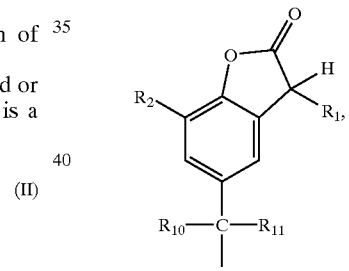

$R_8$ is $C_1$–$C_6$alkyl,
$R_9$ is hydroxy, $C_1$–$C_{18}$alkoxy or

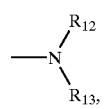

$R_{10}$ and $R_{11}$ are methyl groups or, together with the carbon atom to which they are bonded, form a $C_5$–$C_8$cycloalkylidene ring unsubstituted or substituted by from 1 to 3 $C_1$–$C_4$alkyl groups;
$R_{12}$ and $R_{13}$ are each independently of the other hydrogen or $C_1$–$C_8$alkyl, and
is 2,3,4,5 or 6.

Special preference is given to a process for the preparation of compounds of formula I wherein at least two of the radicals $R_2$, $R_3$, $R_4$ and $R_5$ are hydrogen.

Also very especially preferred is a process for the preparation of compounds of formula I wherein $R_3$ and $R_5$ are hydrogen.

Very special preference is given to a process for the preparation of compounds of formula I wherein $R_2$, $R_3$, $R_4$ and $R_5$ are each independently of the others hydrogen, fluorine, hydroxy, $C_1$–$C_{18}$alkyl, $C_7$–$C_9$phenylalkyl, phenyl, $C_5$–$C_8$cycloalkyl, $C_1$–$C_6$alkoxy, cyclohexylcarbonyloxy or benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —$(CH_2)_p$—$COR_9$, or, when $R_3$ and $R_5$ are hydrogen, $R_4$ is additionally a radical of formula IV, $R_9$ is hydroxy or $C_1$–$C_{18}$alkoxy, and $R_{10}$ and $R_{11}$ are methyl groups or, together with the carbon atom to which they are bonded, form a $C_5$–$C_8$cycloalkylidene ring.

Of preferential interest is a process for the preparation of compounds of formula I wherein $R_2$ is $C_1$–$C_{18}$alkyl or cyclohexyl, $R_3$ is hydrogen, $R_4$ is $C_1$–$C_4$alkyl, cyclohexyl, —$(CH_2)_p$—$COR_9$ or a radical of formula IV, $R_5$ is hydrogen, $R_9$ is $C_1$–$C_4$alkyl, $R_{10}$ and $R_{11}$, together with the carbon atom to which they are bonded, form a cyclohexylidene ring, and p is 2.

Likewise of preferential interest is a process for the preparation of compounds of formula I wherein $R_2$ is $C_1$–$C_8$alkyl or cyclohexyl, $R_3$ is hydrogen, $R'_4$ is $C_1$–$C_4$alkyl, cyclohexyl, —$(CH_2)_p$—$COR_9$ or a radical of formula VI, $R_5$ is hydrogen, $R_9$ is $C_1$–$C_4$alkyl, $R_{10}$ and $R_{11}$, together with the carbon atom to which they are bonded, form a cyclohexylidene ring, and p is 2.

Some of the monomeric compounds of formula V are present in the form of dimers of formula Va.

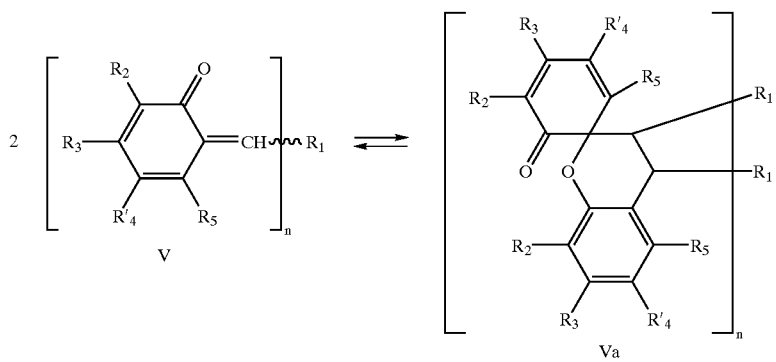

This equilibrium is temperature-dependent. The dimeric compound of formula Va may also be referred to as a Diels-Alder adduct. The dimeric compounds of formula Va can, together with further compounds of formula V, form trimeric, tetrameric or oligomeric compounds.

For the process according to the invention there may be used both the pure monomeric compound of formula V and the pure dimeric compound of formula Va, a mixture of the two compounds of formula V and Va or a mixture of any possible monomeric, dimeric, trimeric or oligomeric compounds derived from the compound of formula V. Under the reaction conditions, the dimeric, trimeric or oligomeric compounds derived from the compound of formula V form again the monomeric compound of formula V, which reacts with carbon monoxide and shifts the equilibrium towards the monomeric side.

Preferred reaction conditions for the process according to the invention are as follows:

The reaction may be carried out at an elevated temperature, especially at temperatures of from 50 to 200° C., in the melt or in a solvent, optionally under slight pressure.

Special preference is given to carrying out the reaction using a large molar excess of carbon monoxide. Special preference is therefore given to a process for the preparation of compounds of formula I wherein the ratio of molar quantities of the compound of formula V to carbon monoxide is from 1:1 to 1:5000.

Preference is given to using, as solvent, pressurised carbon monoxide, which at the same time constitutes the reactant.

As solvents there may, however, also be used solvents that do not participate in the reaction, for example hydrocarbons, ethers and aromatic compounds.

Preferred hydrocarbons are, for example, octane and commercially available isomeric fractions, for example hexane traction, petroleum ether and ligroin.

Preferred ethers are, for example, dibutyl ether, methyl tert-butyl ether and diethylene glycol dimethyl ether.

Examples of aromatic compounds are toluene and xylene.

A preferred catalyst for the process for the preparation of compounds of formula I is a metal catalyst, especially a metal catalyst that is capable of forming a complex with carbon monoxide, for example a transition metal catalyst.

Of preferential interest is a process for the preparation of compounds of formula I wherein the transition metal catalyst is a titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum or copper catalyst. Of special interest is a titanium, vanadium, chromium, manganese, iron, ruthenium, cobalt, rhodium, nickel or palladium catalyst.

Especially preferred catalysts are, for example, $V(CO)_6$; $Cr(CO)_6$; $Mn(CO)_6$; $Mn_2(CO)_{10}$; $Mn(CO)_5Br$; $Fe(CO)_5$; $Fe_2$ (CO)$_9$; Fe$_3$(CO)$_{12}$; Na$_2$Fe(CO)$_4$; [(cyclopentadienyl)Fe(CO)$_2$]$_2$; Co$_2$(CO)$_8$; Co$_4$(CO)$_{12}$; NaCo(CO)$_4$; Ni(CO)$_4$; Ni(CN)$_2$; NiPR'$_3$X'$_2$ wherein R' is unsubstituted substituted phenyl, cyclohexyl or isopropyl and X' is chlorine or bromine; Ni(PPh$_3$)$_2$(CO)$_2$; Pd(PPh$_3$)$_4$; Pd(PR'$_3$)$_2$X''$_2$ wherein R' is as defined above and X'' is chlorine, bromine or iodine; Pd(PPh$_2$Me)$_2$Cl$_2$; Pd(AsPh$_3$)$_2$Cl$_2$; Pd(Br)(Ph)(PPh$_3$)$_2$; Pd(dipp)$_2$ wherein dipp is 1,3-bis(diiso-propylphosphino)propane; PdCl$_2$(R''CN)$_2$ wherein R'' is alkyl or phenyl; Pd(acetate)$_2$+PR'$_3$ wherein R' is as defined above; R'$_2$PCH$_2$CH$_2$CH$_2$PR'$_2$ wherein R' is as defined above; Pd$_2$(di-benzylidene acetone)$_3$+PR'$_3$ wherein R' is as defined above; Li$_2$PdCl$_4$; PdCl$_2$+MgCl$_2$; PdCl$_2$ +CuCl$_2$; HPtCl$_6$; [PtCl$_2$(SnCl$_3$)$_2$]$^{2-}$; [Pt(SnCl$_3$)$_5$]$^{3-}$; Pt(PPh$_3$)$_2$(CO)$_2$; Mo(CO)$_6$; Tc$_2$(CO)$_{10}$; Ru(CO)$_5$; Ru$_3$(CO)$_{12}$; RuCl$_3$; Rh$_2$(CO)$_8$; Rh$_4$(CO)$_{12}$; Rh$_6$(CO)$_{16}$; [Rh(CO)$_2$Cl]$_2$; [Rh(cyclooctadiene)Cl]$_2$; Rh$_2$(acetate)$_4$; Rh(PPh$_3$)$_2$Cl; W(CO)$_6$; Re$_2$(CO)$_{10}$; OS(CO)$_5$; Os$_2$(CO)$_9$; OS$_3$(CO)$_{12}$; Ir$_2$(CO)$_8$ and Ir$_4$(CO)$_{12}$.

A very especially preferred catalyst is, for example, tetrakis(triphenylphosphine)palladium(0).

Advantageously, the catalyst is used in an amount of from 0.01 to 20% by weight, especially from 0.1 to 10% by weight, e.g. from 0.1 to 5% by weight, based on the weight of the compound of formula V used.

The reaction can also be accelerated by addition of a catalytic amount of a protonic acid or Lewis acid.

Suitable protonic acids are, for example, acids of inorganic or organic salts, for example hydrochloric acid, sulfuric acid, phosphoric acid, methanesulfonic acid, p-toluenesultonic acid or carboxylic acids, for example formic acid, acetic acid and trifluoroacetic acid. Special preference is given to formic acid and trifluoroacetic acid.

Suitable Lewis acids are, for example, tin tetrachloride, aluminium chloride, zinc chloride, boron trifluoride etherate or anhydrides, for example carboxylic acid anhydrides, especially acetic anhydride. Special preference is given to tin tetrachloride, aluminium chloride and acetic anhydride.

The starting compounds of formula V are, in some instances, known or can be prepared in analogy to the method described by L. Jurd in *J. Heterocyclic Chem.* 25, 89–96 (1988).

A preferred process for the preparation of the starting compounds of formula V

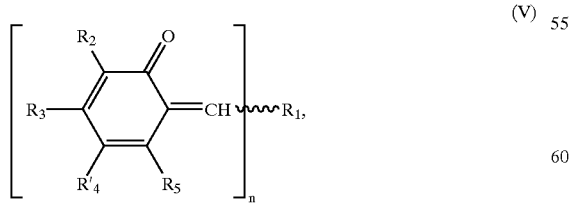
(V)

wherein the general symbols are as defined above, comprises converting a compound of formula VII

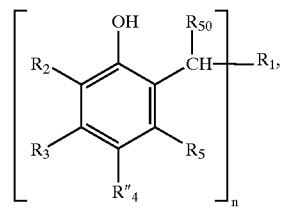
(VII)

wherein R$_1$ and n are as defined above,

R$_2$, R$_3$, R''$_4$ and R$_5$ are each independently of the others hydrogen, fluorine, hydroxy, C$_1$–C$_{25}$alkyl, C$_7$–C$_9$phenylalkyl, unsubstituted or C$_1$–C$_4$alkyl-substituted phenyl, unsubstituted or C$_1$–C$_4$alkyl-substituted C$_5$–C$_8$cycloalkyl; C$_1$–C$_{18}$alkoxy, C$_1$–C$_{18}$alkylthio, C$_1$–C$_4$alkylamino, di(C$_1$–C$_4$alkyl)amino, C$_1$C$_{25}$alkanoyloxy, C$_1$–C$_{25}$alkanoylamino; C$_3$–C$_{25}$alkanoyloxy interrupted by oxygen, sulfur or by

C$_6$–C$_9$cycloalkylcarbonyloxy, benzoyloxy or C$_1$–C$_{12}$alkyl-substituted benzoyloxy, or furthermore the radicals R$_2$ and R$_3$ or the radicals R$_3$ and R''$_4$ or the radicals R''$_4$ and R$_5$, together with the carbon atoms to which they are bonded, form a benzo ring, R''$_4$ is additionally —(CH$_2$)$_p$—COR$_9$ or —(CH$_2$)$_q$OH or, when R$_3$ and R$_5$ are hydrogen, R''$_4$ is additionally a radical of formula VIII

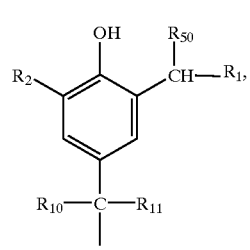
(VIII)

wherein R$_1$ is as defined above for the case where n=1,
R$_2$, R$_{10}$ and R$_{11}$ are as defined above,
R$_{50}$ is —OR$_{51}$, —SR$_{52}$,

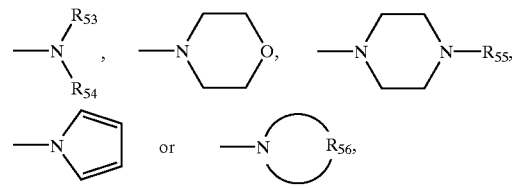

R$_{51}$ is C$_1$–C$_{25}$alkyl; C$_2$–C$_{25}$alkyl interrupted by oxygen or by sulfur; C$_7$–C$_9$phenylalkyl, unsubstituted or C$_1$–C$_4$alkyl-substituted C$_5$–C$_8$cycloalkyl; unsubstituted or C$_1$–C$_4$alkyl-substituted phenyl,
R$_{52}$ is C$_1$–C$_{25}$alkyl; C$_2$–C$_{25}$alkyl interrupted by oxygen or by sulfur; C$_7$–C$_9$phenylalkyl, unsubstituted or $C_1-C_4$alkyl-substituted $C_5-C_8$cycloalkyl; unsubstituted or $C_1-C_4$alkyl-substituted phenyl, $R_{53}$ and $R_{54}$ are each independently of the other hydrogen, $C_1-C_{25}$alkyl; $C_2-C_{25}$alkyl interrupted by oxygen or by sulfur; $C_7-C_9$phenylalkyl, unsubstituted or $C_1-C_4$alkyl-substituted $C_5-C_8$cycloalkyl; or a dendrimeric, oligomeric or polymeric $C_4-C_{100}$hydrocarbon radical, $R_{55}$ is $C_1-C_{25}$alkyl; $C_2-C_{25}$alkyl interrupted by oxygen or by sulfur; $C_7-C_9$phenylalkyl, unsubstituted or $C_1-C_4$alkyl-substituted $C_5-C_8$cycloalkyl; unsubstituted or $C_1-C_4$alkyl-substituted phenyl; or a radical of formula IX

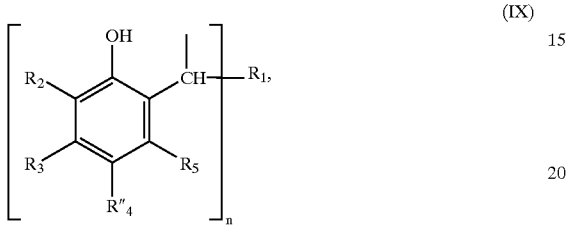

(IX)

wherein $R_1$, $R_2$, $R_3$, $R''_4$, $R_5$ and n are as defined above, $R_{56}$ is unsubstituted or $C_1-C_4$alkyl-substituted $C_2-C_{12}$alkylene, thermally or using light.

In that conversion the radical $HR_{50}$ is removed.

The reaction may be carried out at an elevated temperature, especially at temperatures of from 60 to 180° C., in the melt or in a solvent.

The reaction may be carried out in the melt or in a solvent, optionally under slight pressure.

As solvents there may be used solvents that do not participate in the reaction, for example hydrocarbons, ethers and aromatic compounds.

Preferred hydrocarbons are, for example, octane and commercially available isomeric fractions, for example hexane fraction, petroleum ether and ligroin.

Preferred ethers are, for example, dibutyl ether, methyl tert-butyl ether and diethylene glycol dimethyl ether.

Examples of aromatic compounds are toluene and xylene.

The reaction can also be accelerated by addition of a catalytic to excess amount of a protonic acid.

Suitable protonic acids are, for example, acids of inorganic or organic salts, for example hydrochloric acid, sulfuric acid, phosphoric acid, methanesulfonic acid, p-toluenesulfonic acid or carboxylic acids, for example acetic acid and trifluoroacetic acid. Special preference is given to trifluoroacetic acid.

Preference is given to the process for the preparation of compounds of formula V wherein $R_{50}$ is $-OR_{51}$, $-SR_{52}$,

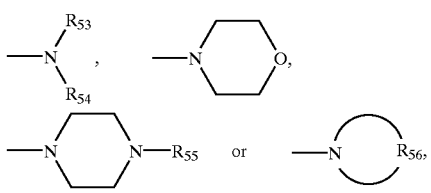

$R_{51}$ is $C_1-C_{12}$alkyl; $C_2-C_2$alkyl interrupted by oxygen; benzyl, $C_5-C_8$cycloalkyl or phenyl, $R_{52}$ is $C_1-C_{12}$alkyl; $C_2-C_{12}$alkyl interrupted by oxygen; benzyl, $C_5-C_8$cycloalkyl or phenyl, $R_{53}$ and $R_{54}$ are each independently of the other hydrogen, $C_1-C_{12}$alkyl; $C_2-C_{12}$alkyl interrupted by oxygen; benzyl, $C_5-C_8$cycloalkyl, or a dendrimeric or oligomeric or polymeric $C_4-C_{50}$hydrocarbon radical, $R_{55}$ is $C_1-C_{12}$alkyl; $C_2-C_{12}$alkyl interrupted by oxygen; benzyl, $C_5$ . $C_8$cycloalkyl, phenyl or a radical of formula IX

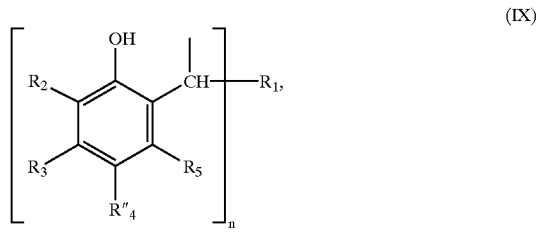

(IX)

wherein $R_1$, $R_2$, $R_3$, $R''_4$, $R_5$ and n are as defined above, and $R_{56}$ is $C_2-C_8$alkylene.

Special preference is given to the process for the preparation of compounds of formula V wherein

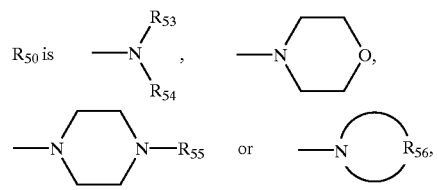

$R_{53}$ and $R_{54}$ are each independently of the other hydrogen, $C_1-C_{12}$alkyl, benzyl, cyclohexyl or a dendrimeric $C_4-C_{30}$hydrocarbon radical, $R_{55}$ is $C_1-C_{12}$alkyl, benzyl, cyclohexyl, phenyl or a radical of formula IX

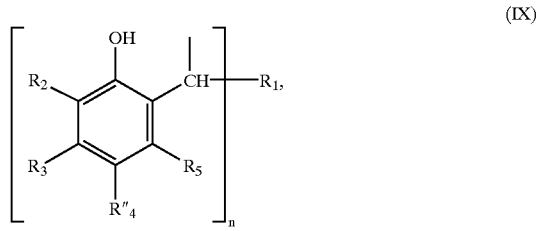

(IX)

wherein $R_1$, $R_2$, $R_3$, $R''_4$, $R_5$ and n are as defined above, and $R_{56}$ is $C_4-C_8$alkylene.

Of special interest is the process for the preparation of compounds of formula V wherein

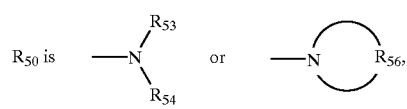

$R_{53}$ and $R_{54}$ are each independently of the other $C_1-C_{12}$alkyl, benzyl or a dendrimeric $C_4-C_{30}$hydrocarbon radical, and $R_{56}$ is $C_4-C_6$alkylene.

Special preference is given to the process for the preparation of compounds of formula V wherein the conversion to the compound of formula V is carried out in the presence of an acid, especially a carboxylic acid, for example acetic acid and trifluoroacetic acid.

The compounds of formula VII are known or can be obtained by methods known per se, such as those disclosed in Examples 1a, 2a and 3a.

The compounds of formula I can also be prepared in a so-called one-pot process, starting from the compounds of formula VII. In that process, the compounds of formula V are prepared in situ and, without being isolated, are reacted further with carbon monoxide in the presence of a catalyst.

The present invention therefore relates also to a process for the preparation of compounds of formula I

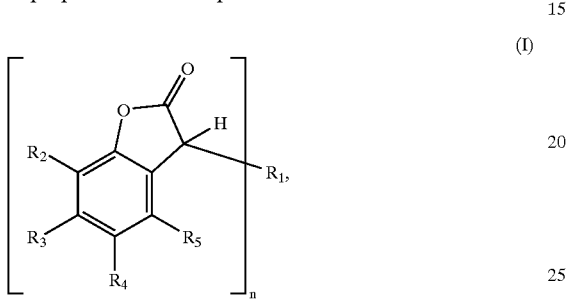

wherein the general symbols are as defined above, which process comprises converting a compound of formula VII

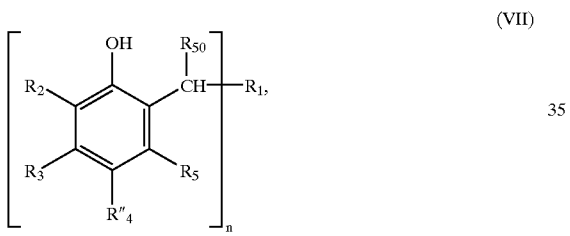

wherein the general symbols are as defined above, thermally or using light, to form a compound of formula V

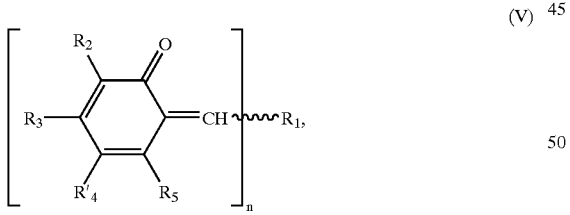

wherein the general symbols are as defined above, and then, without its being isolated, reacting that compound with carbon monoxide in the presence of a catalyst.

The definitions of the general symbols for the one-pot process according to the invention are the same as for the other process of the invention discussed hereinbefore.

The preferred reaction parameters for the one-pot process correspond to the preferences for the two separate steps, which have already been discussed in detail.

The invention relates also to novel compounds of formula V

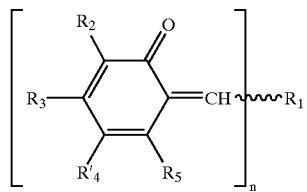

wherein, when n is 1, $R_1$ is naphthyl, phenanthryl, anthryl, 5,6,7,8-tetrahydro-2-naphthyl, thienyl, benzo[b]thienyl, naphtho[2,3-b]thienyl, thianthrenyl, furyl, benzofuryl, isobenzofuryl, dibenzofuryl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by fluorine, hydroxy, $C_1$–$C_{18}$alkyl, $C_1$–$C_{18}$alkoxy, $C_1$–$C_{18}$alkylthio, di($C_1$–$C_4$alkyl)amino, phenyl, benzyl, benzoyl or by benzoyloxy or $R_1$ is a radical of formula II or III

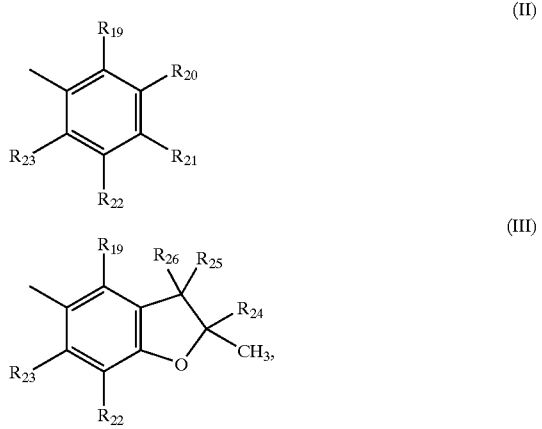

when n is 2, $R_1$ is phenylene or naphthylene each unsubstituted or substituted by $C_3$–$C_4$alkyl or by fluorine, or is —$R_6$—X—$R_7$—, $R_2$, $R_3$, $R'_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R'_4$ or the radicals $R'_4$ and $R_5$, together with the carbon atoms to which they are bonded, form a benzo ring, $R'_4$ is additionally $-(CH_2)_p-COR_9$ or $-(CH_2)_q OH$ or, when $R_3$ and $R_5$ are hydrogen,
$R'_4$ is additionally a radical of formula VI

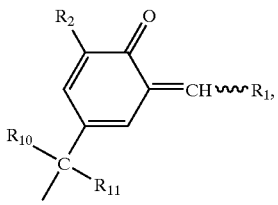

wherein $R_1$ is as defined above for the case where n=1,
$R_6$ and $R_7$ are each independently of the other phenylene or naphthylene each unsubstituted or substituted by $C_1-C_4$alkyl,
$R_8$ is $C_1-C_8$alkyl,
$R_9$ is hydroxy, $$\left[ -O^- \frac{1}{r} M^{r+} \right],$$

$C_1-C_{18}$alkoxy or

$R_{10}$ and $R_{11}$ are each independently of the other hydrogen, $CF_3$, $C_1-C_{12}$alkyl or phenyl, or $R_{10}$ and $R_{11}$, together with the carbon atom to which they are bonded, form a $C_5-C_8$cycloalkylidene ring unsubstituted or substituted by from 1 to 3 $C_1-C_4$alkyl groups;
$R_{12}$ and $R_{13}$ are each independently of the other hydrogen or $C_1-C_{18}$alkyl,
$R_{14}$ is hydrogen or $C_1-C_{18}$alkyl,
$R_{19}$, $R_{20}$, $R_{21}$, $R_{22}$ and $R_{23}$ are each independently of the others hydrogen, fluorine, hydroxy, $C_1-C_{25}$alkyl; $C_2-C_{25}$alkyl interrupted by oxygen, sulfur or by

$C_1-C_{25}$alkoxy; $C_2-C_{25}$alkoxy interrupted by oxygen, sulfur or by

$C_1-C_{25}$alkylthio, $C_7-C_9$phenyl-alkyl, $C_7-C_9$phenylalkoxy, unsubstituted or $C_1-C_4$alkyl-substituted phenyl; unsubstituted or $C_1-C_4$alkyl-substituted phenoxy; unsubstituted or $C_1-C_4$alkyl-substituted $C_5-C_8$cycloalkyl; unsubstituted or $C_1-C_4$alkyl-substituted $C_5-C_8$cycloalkoxy; di($C_1-C_4$alkyl)amino, $C_1-C_{25}$-alkanoyl;

$C_3-C_{25}$alkanoyl interrupted by oxygen, sulfur or by

$C_1-C_{25}$alkanoyloxy; $C_3-C_{25}$alkanoyloxy interrupted by oxygen, sulfur or by

$C_1-C_{25}$alkanoylamino, $C_6-C_9$cycloalkylcarbonyl, $C_6-C_9$cycloalkylcarbonyloxy, benzoyl or $C_1-C_{12}$alkyl-substituted benzoyl; benzoyloxy or $C_1-C_{12}$alkyl-substituted benzoyloxy;

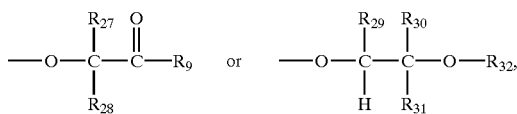

$R_{24}$ is hydrogen, $C_1-C_4$alkyl, or unsubstituted or $C_1-C_4$alkyl-substituted phenyl,
$R_{25}$ and $R_{26}$ are hydrogen, $C_1-C_4$alkyl or phenyl, with the proviso that at least one of the radicals $R_{25}$ and $R_{26}$ is hydrogen,
$R_{27}$ and $R_{28}$ are each independently of the other hydrogen, $C_1-C_4$alkyl or phenyl,
$R_{29}$ is hydrogen or $C_1-C_4$alkyl,
$R_{30}$ is hydrogen, unsubstituted or $C_1-C_4$alkyl-substituted phenyl; $C_1-C_{25}$alkyl; $C_2-C_{25}$alkyl interrupted by oxygen, sulfur or by

$C_7-C_9$phenylalkyl unsubstituted or substituted on the phenyl radical by from 1 to 3 $C_1-C_4$alkyl groups; or $C_7-C_{25}$phenylalkyl interrupted by oxygen, sulfur or by

and unsubstituted or substituted on the phenyl radical by from 1 to 3 $C_1-C_4$alkyl groups,
$R_{31}$ is hydrogen or $C_1-C_4$alkyl,
$R_{32}$ is hydrogen, $C_1-C_{25}$alkanoyl; $C_3-C_{25}$alkanoyl interrupted by oxygen, sulfur or by

$C_2-C_{25}$alkanoyl substituted by a di($C_1-C_6$alkyl) phosphonate group; $C_6-C_9$cycloalkylcarbonyl, thenoyl, furoyl, benzoyl or $C_1-C_{12}$alkyl-substituted benzoyl;

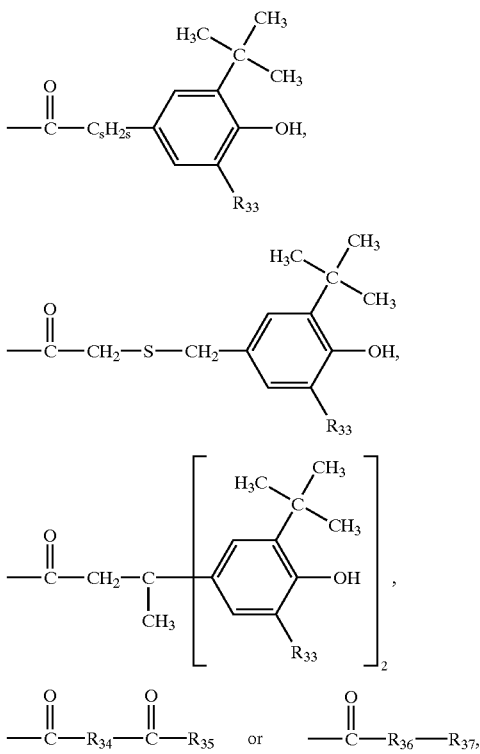

$R_{33}$ is hydrogen or $C_1$–$C_8$alkyl, $R_{34}$ is a direct bond, $C_1$–$C_{18}$alkylene; $C_2$–$C_{18}$alkylene interrupted by oxygen, sulfur or by

$C_2$–$C_{20}$alkylidene, $C_7$–$C_{20}$phenylalkylidene, $C_5$–$C_8$cycloalkylene, $C_7$–$C_8$bicyclo-alkylene, unsubstituted or $C_1$–$C_4$alkyl-substituted phenylene,

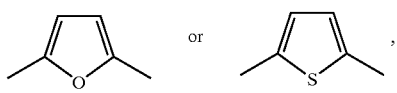

$R_{35}$ is hydroxy,

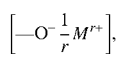

$C_1$–$C_{18}$alkoxy or

$R_{36}$ is oxygen, —NH— or

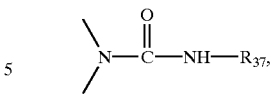

$R_{37}$ is $C_1$–$C_{18}$alkyl or phenyl,

M is an r-valent metal cation,

X is a direct bond, oxygen, sulfur or —$NR_{14}$—, n is 1 or 2, p is 0, 1 or 2, q is 1, 2,3,4,5 or 6, r is 1, 2 or 3, and s is 0, 1 or 2, with the proviso that when $R_2$ and $R'_4$ are hydrogen, methyl or tert-butyl or when $R_3$ and $R'_4$, together with the carbon atom to which they are bonded, form a benzo ring, at least one of the radicals $R_{19}$, $R_{20}$, $R_{21}$, $R_{22}$ and $R_{23}$ is other than hydrogen and $R_1$ is not unsubstituted naphthyl; with the proviso that $R_{19}$ and $R_{23}$ are other than hydroxy; and with the proviso that when $R_2$ and $R'_4$ are hydrogen, $C_1$–$C_4$alkyl or methoxy, $R_{20}$, $R_{21}$ and $R_{22}$ are other than methoxy.

The preferred general symbols for the novel compounds of formula V correspond to those in the preferred general symbols set out hereinbefore for the process according to the invention for the preparation of compounds of formula I.

The following Examples illustrate the invention further. Parts or percentages relate to weight.

EXAMPLE 1

Process for the Preparation of 5,7-di-tert-butyl-3-(3, 4-dimethyl-phenyl)-3H-benzofuran-2-one (compound (101), Table 1).

a) Preparation of 2,4-di-tert-butyl-6-[dimethylamino-(3,4-dimethyl-phenyl)-methyl]-phenol (compound (201), Table 2).

A mixture of 26.82 g (0.13 mol) of 2,4-di-tert-butylphenol, 17.44 g (0.13 mol) of 3,4-dimethylbenzaldehyde and 22.0 g (0.20 mol) of a 40% aqueous solution of dimethylamine is heated in a closed vessel at 140° C. for 10 hours, the internal pressure rising to 4 bar. After cooling to room temperature, the reaction mixture is poured into 100 ml of water and extracted twice using ethyl acetate. The organic phases are combined, dried over sodium sulfate and concentrated using a vacuum rotary evaporator. Crystallisation of the residue from isopropanol yields 28.25 g (59%) of 2,4-di-tert-butyl-6-[dimethylamino-(3,4-dimethyl-phenyl)-methyl]-phenol, m.p. 82–85° C., (compound (201), Table 2). Molecular weight $C_{25}H_{37}NO$ (367.58). Analysis, calculated: C 81.69; H 10.15; N 3.81%. Analysis, found: C 81.78; H 10.05; N 3.80%. $^1$HNMR (300 MHz, $CDCl_3$, ppm): 1.18 (s, 9H); 1.43 (s, 9H); 221 (s, 6H); 2.24 (s, 6H); 4.27 (s, 1H); 6.74 (d, 1H); 7.11 (m, 4H); 12.43 (s, 1H).

b) Preparation of 2,4-di-tert-butyl-6-(3,4-dimethylbenzylidene)-cyclohexa-2,4-dienone (compound (301), Table 3) and the corresponding dimer (compound (401), Table 4).

60 ml of dry toluene and 2.9 g (25.5 mmol) of trifluoroacetic acid are added, under argon, to 6.24 g (17 mmol) of 2,4-di-tert-butyl-6-[dimethylamino-(3,4-dimethyl-pheny)-methyl]-phenol (compound (201), Table 2), prepared according to Example 1a. The reaction mixture is then maintained at 110° C. for 6 hours. After cooling to room temperature, the mixture is poured into 50 ml of water and extracted three times using ethyl acetate. The organic phases are combined, dried over sodium sulfate and concentrated using a vacuum rotary evaporator. Crystallisation of the residue from isopropanol yields 4.48 g (82%) of a mixture of 2,4-di-tert-butyl-6-(3,4-dimethyl-benzylidene)-cyclohexa-2,4-dienone (compound (301), Table 3) and the corresponding dimer (compound (401), Table 4), m.p. 214–217° C.

b') Alternative process for the preparation of 2,4-di-tert-butyl-6-(3,4-dimethylbenzylidene)-cyclohexa-2,4-dienone (compound (301), Table 3) and the corresponding dimer (compound (401), Table 4).

A solution of 33.85 g (0.10 mol) of 3,5-di-tert-butyl-2-hydroxy-phenyl-(3,4-dimethyl-phenyl)-methanone (compound (203), Table 2) in 130 ml of dry tetrahydrofuran is slowly added dropwise, at 10° C., to a suspension of 7.57 g (0.20 mol) of lithium aluminium hydride in 150 ml of dry tetrahydrofuran, during which the reaction temperature should not exceed 15° C. After the addition, the reaction mixture is stirred for a further 30 minutes at room temperature. The excess of lithium aluminium hydride is destroyed by means of basic hydrolysis and the salts formed are filtered off. The residue is washed with tetrahydrofuran and the filtrates are concentrated using a vacuum rotary evaporator. The crude alcohol (compound (204), Table 2) is taken up in 100 ml of isopropanol; 0.2 g (1.05 mmol) of p-toluenesulfonic acid is added and the mixture is boiled under reflux for 18 hours. The reaction mixture is then concentrated using a vacuum rotary evaporator. Crystallisation of the residue from isopropanol yields 17.11 g (53%) of a mixture of 2,4-di-tert-butyl-6-(3,4-dimethyl-benzylidene)-cyclohexa-2,4-dienone (compound (301), Table 3) and the corresponding dimer (compound (401), Table 4), m.p. 214–217° C.

c) Preparation of 5,7-di-tert-butyl-3-(3,4-dimethyl-phenyl)-3H-benzofuran-2-one (compound (101), Table 1).

A solution of 645 mg (2.0 mmol) of a mixture of 2,4-di-tert-butyl-6-(3,4-dimethyl-benzylidene)-cyclohexa-2,4-dienone (compound (301). Table 3) and the corresponding dimer (compound (401), Table 4), prepared according to Example 1b, in 7 ml of toluene is degassed using argon and then 58 mg (0.05 mmol) of tetrakis(triphenylphosphine)-palladium(0) and 23 mg (0.20 mmol) of trifluoroacetic acid are added. The autoclave is flushed with carbon monoxide and sealed, and a carbon monoxide pressure of 5 bar is then applied. The reaction mixture is maintained at 80° C. for 20 hours. After cooling to room temperature, the reaction mixture is poured into water and extracted three times using ethyl acetate. The organic phases are combined, dried over sodium sulfate and concentrated using a vacuum rotary evaporator. Crystallisation of the residue from ethanol yields 464 mg (66%) of 5,7-di-tert-butyl-3-(3,4-dimethyl-phenyl)-3H-benzofuran-2-one (compound (101), Table 1), m.p. 130–132° C. Analysis, calculated: C 82.24; H 8.63%. Analysis, found: C 82.20; H 8.68%.

EXAMPLE 2

Process for the Preparation of 5,7-di-tert-butyl-3-phenyl-3H-benzofuran-2-one (compound (102), Table 1).

a) Preparation of 2,4-di-tert-butyl-6-(dimethylamino-phenyl-methyl)-phenol (compound (202), Table 2).

A mixture of 51.5 g (0.25 mol) of 2,4-di-tert-butylphenol, 26.5 g (0.25 mol) of benzaldehyde and 42.3 g (0.375 mol) of a 40% aqueous solution of dimethylamine is heated in a closed vessel at 140° C. for 10 hours, the internal pressure rising to 5 bar. After cooling to room temperature, the reaction mixture solidifies. Crystallisation of the residue from isopropanol yields 65.2 g (77%) of 2,4-di-tert-butyl-6-(dimethylamino-phenyl-methyl)-phenol, m.p. 120–123° C. (compound (202), Table 2). Molecular weight $C_{23}H_{33}NO$ (339.52). Analysis, calculated: C 81.37; H 9.80; N 4.13%. Analysis, found: C 81.25; H 9.86; N 4.00%. $^1$HNMR (300 MHz, $CDCl_3$, ppm): 1.19 (s, 9H); 1.44 (s, 9H); 2.26 (s, 6H); 4.34 (s, 1H); 6.75 (d, 1H); 7.29 (m, 6H); 12.43 (s, 1H).

b) Preparation of 6-benzylidene-2,4-di-tert-butyl-cyclohexa-2,4-dienone (compound (302), Table 3) and the corresponding dimer (compound (402), Table 4).

60 ml of dry toluene and 2.9 g (25.5 mmol) of trifluoroacetic acid are added, under argon, to 5.75 g (17 mmol) of 2,4-di-tert-butyl-6-(dimethylamino-phenyl-methyl)-phenol (compound (202), Table 2), prepared according to Example 2a. The reaction mixture is then maintained at 110° C. for 6 hours. After cooling to room temperature, the mixture is poured into 50 ml of water and extracted three times using ethyl acetate. The organic phases are combined, dried over sodium sulfate and concentrated using a vacuum rotary evaporator. Crystallisation of the residue from acetonitrile yields 2.58 g (52%) of a mixture of 6-benzylidene-2,4-di-tert-butyl-cyclohexa-2,4-dienone (compound (302), Table 3) and the corresponding dimer (compound (402), Table 4), m.p. 164–166° C. Analysis, calculated for (302) and (402): C 85.67; H 8.90%. Analysis, found for (302) and (402): C 85.36; H 8.93%.

c) Preparation of 5,7-di-tert-butyl-3-phenyl-3H-benzofuran-2-one (compound (102), Table 1).

A solution of 589 mg (2.0 mmol) of a mixture of 6-benzylidene-2,4-di-tert-butyl-cyclohexa-2,4-dienone (compound (302), Table 3) and the corresponding dimer (compound (402), Table 4), prepared according to Example 2b, in 7 ml of toluene is degassed using argon and then 58 mg (0.05 mmol) of tetrakis(triphenylphosphine)palladium (0) and 23 mg (0.20 mmol) of trifluoroacetic acid are added. The autoclave is flushed with carbon monoxide and sealed, and a carbon monoxide pressure of 5 bar is then applied. The reaction mixture is maintained at 80° C. for 20 hours. After cooling to room temperature, the reaction mixture is poured into water and extracted three times using ethyl acetate. The organic phases are combined, dried over sodium sulfate and concentrated using a vacuum rotary evaporator. Crystallisation of the residue from isopropanol yields 580 mg (90%) of 5,7-di-tert-butyl-3-phenyl-3H-benzofuran-2-one (compound (102), Table 1), m.p. 116–119° C. Analysis, calculated: C 81.95; H 8.13%. Analysis, found: C 81.93; H 8.13%.

EXAMPLE 3

One-pot Process for the Preparation of Compound (103) (Table 1), Starting from Compound (205) (Table 2).

a) Preparation of compound (205) (Table 2).

A mixture of 45.67 g (0.12 mol) of 1,1'-bis[4,4'-(2-tert-butyl-1-hydroxy-phenyl)]cyclohexane, 25.5 g (0.24 mol) of benzaldehyde and 40.6 g (0.36 mol) of a 40% aqueous solution of dimethylamine is heated in a closed vessel at 140° C. for 10 hours, the internal pressure rising to 4.5 bar. After cooling to room temperature, the reaction mixture solidifies. Crystallisation of the residue from isopropanol yields 64.3 g (83%) of compound (205) (Table 2), m.p. 156–159° C. Molecular weight $C_{44}H58N_2O_2$ (646.96). Analysis, calculated: C 81.69; H 9.04; N 4.33%. Analysis, found: C 81.46; H 9.05; N 4.18%.

b) One-pot process for the preparation of compound (103) (Table 1), starting from compound (205) (Table 2).

A solution of 6.47 g (0.01 mol) of compound (205), prepared according to Example 3a, in 60 ml of dry toluene is degassed using argon and then 0.87 g (0.75 mmol) of tetrakis(triphenylphosphine)palladium(0) and 3.43 g (0.03 mol) of trifluoroacetic acid are added. The autoclave is flushed with carbon monoxide and sealed, and a carbon monoxide pressure of 7.5 bar is then applied. The reaction mixture is maintained at 140° C. for 18 hours. After cooling to room temperature, the reaction mixture is poured into water and extracted three times using ethyl acetate. The organic phases are combined, dried over sodium sulfate and concentrated using a vacuum rotary evaporator. Crystallisation of the residue from isopropanol yields 4.30 g (70%) of compound (103) (Table 1), m.p. 199–202° C. Empirical formula $C_{42}H_{44}O_4$. Analysis, calculated: C 82.32; H 7.24%. Analysis, found: C 81.91; H 7.20% $^1$HNMR (300 MHz, $CDCl_3$, ppm): 1.34 (s, 18H); 1.48 (m, 6H); 2.17 (m, 4H); 4.80 (s, 2H); 6.94 (s, 2H); 7.14 (m, 6H); 7.29 (m, 6H).

EXAMPLE 4

One-pot Process for the Preparation of Compound (102) (Table 1), Starting from Compound (202) (Table 2).

A solution of 640 mg (1.89 mmol) of compound (202), prepared according to Example 2a, in 10 ml of dry toluene is degassed using argon and then 55 mg (0.05 mmol) of tetrakis(triphenylphosphine)palladium(0) and 323 mg (2.83 mmol) of trifluoroacetic acid are added. The autoclave is flushed with carbon monoxide and sealed, and a carbon monoxide pressure of 8 bar is then applied. The reaction mixture is maintained at 140° C. for 19 hours. After cooling to room temperature, the reaction mixture is poured into water and extracted three times using ethyl acetate. The organic phases are combined, dried over sodium sulfate and concentrated using a vacuum rotary evaporator. Filtration of the residue on silica gel using ethyl acetate and crystallisation of the pure fractions from isopropanol yields 561 mg (92%) of compound (102) (Table 1), m.p. 116–119° C. Analysis, calculated: C 81.95; H 8.13%. Analysis, found: C 81.90; H 8.15%.

Compound (102) (Table 1) may also be obtained in analogy to Example 4 using acetic anhydride instead of trifluoroacetic acid.

EXAMPLE 5

Process for the Preparation of Compound (104), Table 1.
a) Preparation of compound (206), Table 2.

Compound (206), Table 2, m.p. 205–206° C., is obtained in analogy to Example 1a using 0.065 mol of terephthaldehyde (Fluka 86410) instead of 3,4-dimethylbenzaldehyde. Molecular weight $C_{40}H_{60}N_2O_2$ (600.932). Analysis, calculated: C 79.95; H 10.06; N 4.66%. Analysis, found: C 80.22; H 10.01; N 4.70%. $^1$HNMR (300 MHz, $CDCl_3$, ppm): 1.16 (s, 18H); 1.41 (s, 18H); 2.21 (s, 12H); 4.27 (s, 2H); 6.69 (d, 2H); 7.13 (d, 2H); 7.35 (s, 4H); 12.38 (s, 2H).
b) Preparation of compound (104), Table 1.

A solution of 1.14 g (1.89 mmol) of compound (206), prepared according to Example 5a, in 10 ml of dry toluene is degassed using argon and then 55 mg (0.05 mmol) of tetrakis(triphenylphosphine)palladium(0) and 348 mg (7.56 mmol) of formic acid are added. The autoclave is flushed with carbon monoxide and sealed, and a carbon monoxide pressure of 8 bar is then applied. The reaction mixture is maintained at 110° C. for 4 hours. After cooling to room temperature, the reaction mixture is poured into water and extracted three times using ethyl acetate. The organic phases are combined, dried over sodium sulfate and concentrated using a vacuum rotary evaporator. Filtration of the residue on silica gel using ethyl acetate and crystallisation of the pure fractions from isopropanol yields 942 mg (88%) of compound (104) (Table 1), m.p. 212–215° C. Molecular weight $C_3H_{46}O_4$ (566.784). $^1$HNMR (300 MHz, $CDCl_3$, ppm): 1.28 (s, 18H); 1.42 (s, 18H): 4.82 (s, 2H); 7.05 (d, 2H); 7.25 (s, 4H); 7.32 (d, 2H).

EXAMPLE 6

Process for the Preparation of Compound (102), Table 1.
a) Preparation of compound (208), Table 2.

37.46 g (0.44 mol) of piperidine are added dropwise, at room temperature, to a solution of 21.22 g (0.20 mol) of benzaldehyde in 70 ml of toluene; slight exothermicity is observed. The slightly yellow-coloured solution is boiled under reflux for 2 hours; approximately 4 ml of water are separated off using a water separator, and a solution of 39.20 g (0.19 mol) of 2,4-di-tert-butylphenol in 30 ml of toluene is then added dropwise. The reaction mixture is boiled at reflux for a further hour and then cooled to room temperature; the solvent is distilled off using a vacuum rotary evaporator. Crystallisation of the residue from toluene yields 50.14 g (70%) of compound (208) (Table 2), m.p. 140–141° C. Molecular weight $C_{26}H_{37}NO$ (379.588). Analysis, calculated: C 82.27; H 9.82; N 3.69%. Analysis, found: C 82.06; H 9.83; N 3.77%. $^1$HNMR (300 MHz, $CDCl_3$, ppm): 1.24 (s, 9H); 1.50 (s, 11H); 1.66 (bs, 4H); 2.39 (bs, 4H); 4.48 (s, 1H); 6.79 (d, 1H); 7.32 (m, 6H); 12.60 (s, 1H).
b) Preparation of compound (102), Table 1.

Compound (102), Table 1, m.p. 116–119° C., is obtained in analogy to Example 4 using compound (208), prepared according to Example 6a, instead of compound (202).

EXAMPLE 7

Process for the Preparation of Compound (105), Table 1.
a) Preparation of compound (207), Table 2.

8.29 g (97.33 mmol) of piperidine are added dropwise, at room temperature, to a solution of 4.71 g (44.43 mmol) of benzaldehyde in 50 ml of toluene; slight exothermicity is observed. The slightly yellow-coloured solution is boiled under reflux for 15 hours; approximately 1 ml of water is separated off using a water separator, and a solution of 10.0 g (42.3 mmol) of 3-(3-tert-butyl-4-hydroxy-phenyl)-propionic acid methyl ester in 15 ml of toluene is then added dropwise. The reaction mixture is boiled at reflux for a further hour and then cooled to room temperature; the solvent is distilled off using a vacuum rotary evaporator. Filtration of the residue over silica gel using ethyl acetate and crystallisation of the pure fractions from hexane yields 12.31 g (71%) of compound (207) (Table 2), m.p. 120–122° C. Molecular weight $C_{26}H_{35}NO_3$ (409.571). Analysis, calculated: C 76.25; H 8.61; N 3.42%. Analysis, found: C76.18; H 8.73; N 3.35%. $^1$HNMR (300 MHz, $CDCl_3$, ppm): 1.36 (s, 9H); 1.46 (m, 6H); 2.37 (bm, 4H); 2.41 (m, 2H) 2.66 (m, 2H); 3.53 (s, 3H); 4.33 (s, 2H); 6.49 (d, 1H); 6.86 (d,1 H); 7.23 (m, 5H); 12.60 (s, 1 H).
b) Preparation of compound (105), Table 1.

Compound (105), Table 1, is obtained as a slightly yellow oil, in analogy to Example 5 using compound (207), prepared according to Example 7a, instead of compound (206). Molecular weight $C_{22}H_{24}O_4$ (352.432). Analysis, calculated: C 74.98; H 6.86%. Analysis, found: C 75.08; H 6.89%. $^1$HNMR (300 MHz, $CDCl_3$, ppm): 1.35 (s, 9H); 2.52 (t, 2H); 2.84 (t, 2H); 3.56 (s, 3H); 4.75 (s, 1H); 6.80 (d, 1H); 7.04 (d, 1H); 7.14 (m, 2H); 7.29 (m, 3H).

TABLE 1

| no. | compound |
|-----|----------|
| 101 | (3-(3,4-dimethylphenyl)-5,7-di-tert-butyl-benzofuran-2(3H)-one) |
| 102 | (5,7-di-tert-butyl-3-phenyl-benzofuran-2(3H)-one) |
| 103 | (bis-benzofuranone linked via cyclohexylidene bridge; each benzofuranone bearing 7-tert-butyl and 3-phenyl substituents) |
| 104 | (bis(5,7-di-tert-butyl-3H-benzofuran-2-one) linked at the 3-positions through a 1,4-phenylene bridge) |
| 105 | (7-tert-butyl-3-phenyl-5-(2-(methoxycarbonyl)ethyl)-benzofuran-2(3H)-one) |

TABLE 2
| no. | compound |
|---|---|
| 201 | 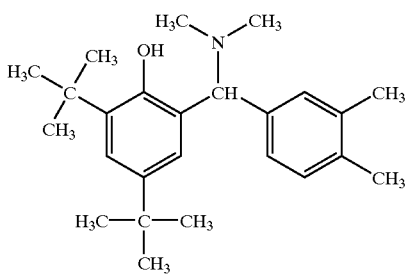 |
| 202 | 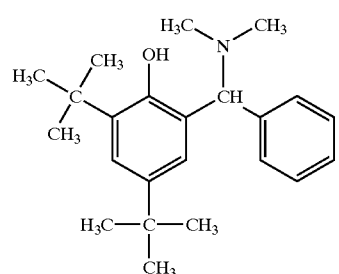 |
| 203 | 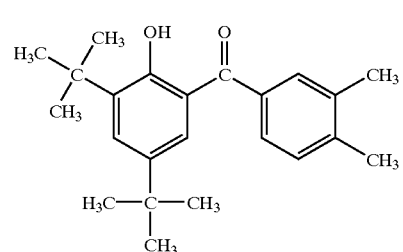 |
| 204 | 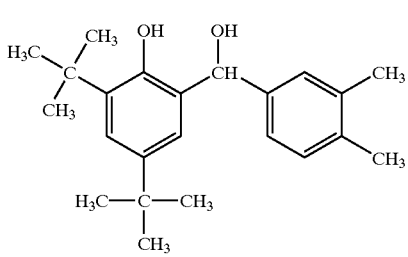 |
| 205 | 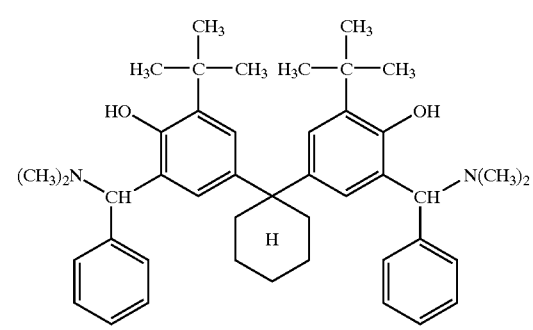 |

TABLE 2-continued

| no. | compound |
|---|---|
| 206 | (structure) |
| 207 | (structure) |
| 208 | (structure) |

TABLE 3

| no. | compound |
|---|---|
| 301 | (structure) |
| 302 | (structure) |

TABLE 4

| no. | compound |
|-----|----------|
| 401 | 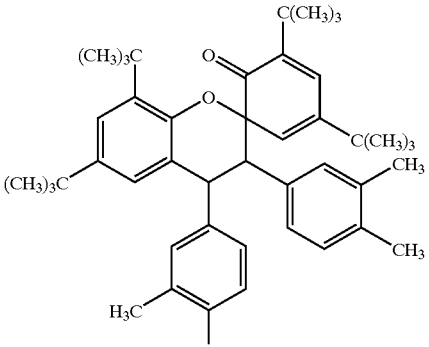 |
| 402 | 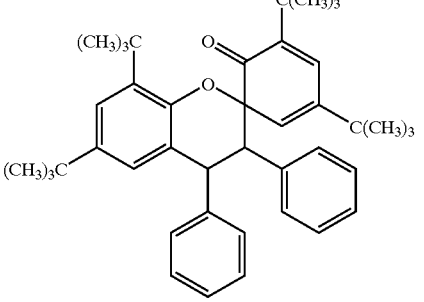 |

EXAMPLE 8

One-pot Process for the Preparation of Compound (102) (Table 1), Starting from Compound (202) (Table 2) using Various Catalysts.

A solution of 640 mg (1.89 mmol) of compound (202), prepared according to Example 2a, in 10 ml of dry toluene is degassed using argon, and the catalyst given in the Table and 348 mg (7.56 mmol) of formic acid are then added. The autoclave is flushed with carbon monoxide and sealed, and a carbon monoxide pressure of 8 bar is then applied. The reaction mixture is maintained at 110° C. for 4 hours. After cooling to room temperature, the reaction mixture is poured into water and extracted three times using ethyl acetate. The organic phases are combined, dried over sodium sulfate and concentrated using a vacuum rotary evaporator. Filtration of the residue on silica gel using ethyl acetate and crystallisation of the pure fractions from isopropanol yields compound (102) (Table 1), m.p. 116–119° C. The results are collated in Table 5.

TABLE 5

| Ex. | catalyst | amount of catalyst [mol %] | yield of compound (102) in % |
|-----|----------|----------------------------|------------------------------|
| 8a  | Pd(PPh$_3$)$_4$ | 2.5 | 92 |
| 8b  | Pd(OAc)$_2$/2PPh$_3$ | 2.5 | 99 |
| 8c  | Pd(OAc)$_2$/2PPh$_3$ | 0.25 | 82 |
| 8d  | 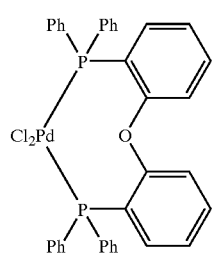 | 0.1 | 70 |

TABLE 5-continued

| Ex. | catalyst | amount of catalyst [mol %] | yield of compound (102) in % |
|---|---|---|---|
| 8e | (tricyclopentylphosphine)₂PdCl₂ | 0.1 | 80 |
| 8f | (tricyclohexylphosphine)₂PdCl₂ | 0.1 | 90 |
| 8g | [1,3-bis(diphenylphosphino)propane]PdCl₂ | 0.1 | 90 |
| 8h | (ferrocenyl ligand with PH₂ and PCy₂)PdCl₂ | 0.1 | 90 |
| 8k | [1,1'-bis(diphenylphosphino)ferrocene]PdCl₂ | 0.1 | 90 |

TABLE 5-continued

| Ex. | catalyst | amount of catalyst [mol %] | yield of compound (102) in % |
|---|---|---|---|
| 8l | 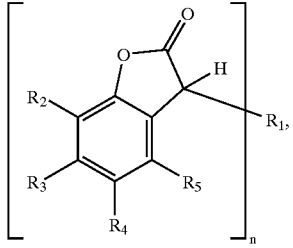 | 0.1 | 95 |
| 8m | 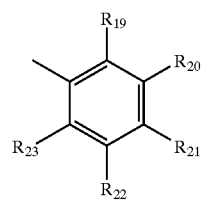 | 0.1 | 95 |
| 8n | 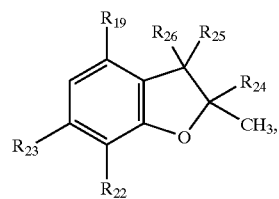 1 equivalent of PdCl₂ (solution in water/HCl/ dimethyl acetamide) | 0.1 | 95 |

What is claimed is:

1. A process for the preparation of compounds of formula I $$\left[ \begin{array}{c} \text{structure with } R_2, R_3, R_4, R_5 \text{ on benzofuranone with } R_1, H \end{array} \right]_n \quad (I)$$

wherein, when n is 1, $R_1$ is naphthyl, phenanthryl, anthryl, 5,6,7,8-tetrahydro-2-naphthyl, thienyl, benzo[b]thienyl, naphtho[2,3-b]thienyl, thianthrenyl, furyl, benzofuryl, isobenzofuryl, dibenzofuryl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by fluorine, hydroxy, $C_1$–$C_{18}$alkyl, $C_1$–$C_{18}$alkoxy, $C_1$–$C_{18}$ alkylthio, di-($C_1$–$C_4$alkyl)amino, phenyl, benzyl, benzoyl or by benzoyloxy or $R_1$ is a radical of formula II or III $$\text{(II) structure with } R_{19}, R_{20}, R_{21}, R_{22}, R_{23}$$

$$\text{(III) structure with } R_{19}, R_{26}, R_{25}, R_{24}, CH_3, R_{23}, R_{22}$$

when n is 2, $R_1$ is phenylene or naphthylene each unsubstituted or substituted by $C_1$–$C_4$alkyl or by fluorine; or is —$R_6$—X—$R_7$—, $R_2$, $R_3$, $R_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —$(CH_2)_p$—$COR_9$ or —$(CH_2)_q$OH or, when $R_3$ and $R_5$ are hydrogen, $R_4$ is additionally a radical of formula IV

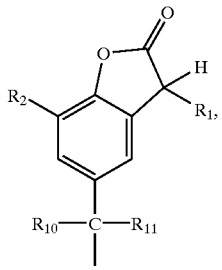

(IV)

wherein $R_1$ is as defined above for the case where n=1, $R_6$ and $R_7$ are each independently of the other phenylene or naphthylene each unsubstituted or substituted by $C_1$–$C_4$alkyl, $R_8$ is $C_1$–$C_8$alkyl, $R_9$ is hydroxy,

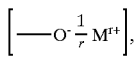

$C_1$–$C_{18}$alkoxy or

$R_{10}$ and $R_{11}$ are each independently of the other hydrogen, $CF_3$, $C_1$–$C_{12}$alkyl or phenyl, or $R_{10}$ and $R_{11}$, together with the carbon atom to which they are bonded, form a $C_5$–$C_8$cycloalkylidene ring unsubstituted or substituted by from 1 to 3 $C_1$–$C_4$alkyl groups;

$R_{12}$ and $R_{13}$ are each independently of the other hydrogen or $C_1$–$C_{18}$alkyl, $R_{14}$ is hydrogen or $C_1$–$C_{18}$alkyl, $R_{19}$, $R_{20}$, $R_{21}$, $R_{22}$ and $R_{23}$ are each independently of the others hydrogen, fluorine, hydroxy, $C_1$–$C_{25}$alkyl; $C_2$–$C_{25}$alkyl interrupted by oxygen, sulfur or by

$C_1$–$C_{25}$alkoxy; $C_2$–$C_{25}$alkoxy interrupted by oxygen, sulfur or by

$C_1$–$C_{25}$alkylthio, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; di($C_1$–$C_4$alkyl)amino, $C_1$–$C_{25}$-alkanoyl; $C_3$–$C_{25}$alkanoyl interrupted by oxygen, sulfur or by

$C_1$–$C_{25}$alkanoyloxy; $C_3$–$C_{25}$alkanoyloxy interrupted by oxygen, sulfur or by

$C_1$–$C_{25}$alkanoylamino, $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

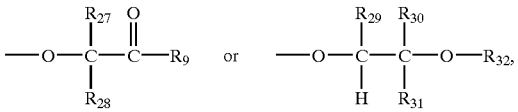

$R_{24}$ is hydrogen, $C_1$–$C_4$alkyl, or unsubstituted or $C_1$–$C_4$alkyl-substituted phenyl, $R_{25}$ and $R_{26}$ are hydrogen, $C_1$–$C_4$alkyl or phenyl, with the proviso that at least one of the radicals $R_{25}$ and $R_{26}$ is hydrogen, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{25}$alkyl; $C_2$–$C_{25}$alkyl interrupted by oxygen, sulfur or by

$C_7$–$C_9$phenylalkyl unsubstituted or substituted on the phenyl radical by from 1 to 3 $C_1$–$C_4$alkyl groups; or $C_7$–$C_{25}$phenylalkyl interrupted by oxygen, sulfur or by

and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{25}$alkanoyl; $C_3$–$C_{25}$alkanoyl interrupted by oxygen, sulfur or by

$C_2$–$C_{25}$alkanoyl substituted by a di($C_1$–$C_6$alkyl) phosphonate group; $C_6$–$C_9$-cycloalkylcarbonyl, thenoyl, furoyl, benzoyl or $C_1$–$C_{12}$alkyl-substituted benzoyl;

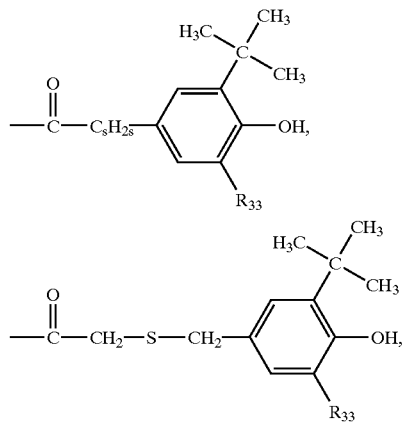

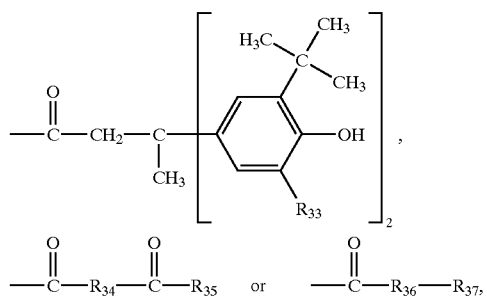

$R_{33}$ is hydrogen or $C_1$–$C_8$alkyl, $R_{34}$ is a direct bond, $C_1$–$C_{18}$alkylene; $C_2$–$C_{18}$alkylene interrupted by oxygen, sulfur or by

$C_2$–$C_{20}$alkylidene, $C_7$–$C_{20}$phenylalkylidene, $C_5$–$C_8$cycloalkylene, $C_7$–$C_8$bicyclo-alkylene, unsubstituted or $C_1$–$C_4$alkyl-substituted phenylene,

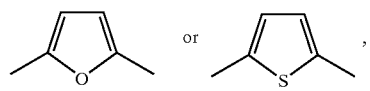

$R_{35}$ is hydroxy,

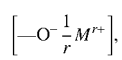

$C_1$–$C_{18}$alkoxy or

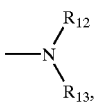

$R_{36}$ is oxygen, —NH— or

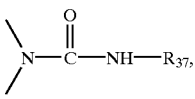

$R_{37}$ is $C_1$–$C_{18}$alkyl or phenyl,

M is an r-valent metal cation,

X is a direct bond, oxygen, sulfur or —$NR_{14}$—, n is 1 or 2, p is 0, 1 or 2, q is 1, 2, 3, 4, 5 or 6, r is 1, 2 or 3, and s is 0, 1 or 2, which process comprises reacting a compound of formula V

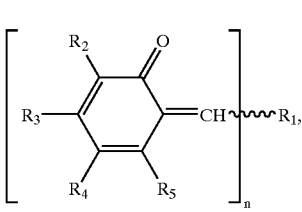

(V)

wherein $R_1$ and n are as defined above, $R_2$, $R_3$, $R'_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$-cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R'_4$ or the radicals $R'_4$ and $R_5$, together with the carbon atoms to which they are bonded, form a benzo ring, $R'_4$ is additionally —$(CH_2)_p$—$COR_9$ or —$(CH_2)_q$OH or, when $R_3$ and $R_5$ are hydrogen, $R'_4$ is additionally a radical of formula VI

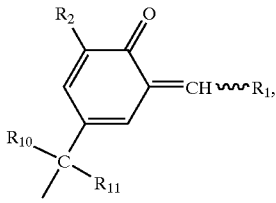

(VI)

wherein $R_1$ is as defined above for the case where n=1, with carbon monoxide in the presence of a catalyst.

2. A process according to claim 1, wherein, when n is 2, $R_1$ is phenylene or —$R_6$—X—$R_7$—, $R_6$ and $R_7$ are phenylene, X is oxygen or —$NR_{14}$—, and $R_{14}$ is $C_1$–$C_4$alkyl.

3. A process according to claim 1, wherein $R_{19}$, $R_{20}$, $R_{21}$, $R_{22}$ and $R_{23}$ are each independently of the others hydrogen, fluorine, hydroxy, $C_1$–$C_{18}$alkyl; $C_2$–$C_{18}$alkyl interrupted by oxygen or by sulfur; $C_1$–$C_{18}$alkoxy; $C_2$–$C_{18}$alkoxy interrupted by oxygen or by sulfur; $C_1$–$C_{18}$alkylthio, $C_7$–$C_9$phenylalkyl, $C_7$–$C_9$phenylalkoxy, unsubstituted or $C_1$–$C_4$alkyl substituted phenyl; phenoxy, cyclohexyl, $C_5$–$C_8$cycloalkoxy, di($C_1$–$C_4$-alkyl)amino, $C_1$–$C_{12}$alkanoyl; $C_3$–$C_{12}$alkanoyl interrupted by oxygen or by sulfur; $C_1$–$C_{12}$alkanoyloxy; $C_3$–$C_{12}$alkanoyloxy interrupted by oxygen or by sulfur; $C_1$–$C_{12}$alkanoylamino, cyclohexylcarbonyl, cyclohexylcarbonyloxy, benzoyl or $C_1$–$C_4$alkyl-substituted benzoyl; benzoyloxy or $C_1$–$C_4$alkyl-substituted benzoyloxy;

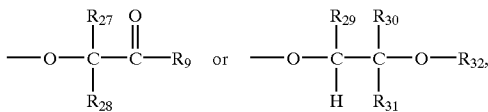

$R_{24}$ is hydrogen or $C_1$–$C_4$alkyl, $R_{25}$ and $R_{26}$ are hydrogen or $C_1$–$C_4$alkyl, with the proviso that at least one of the radicals $R_{25}$ and $R_{26}$ is hydrogen, $R_{27}$ and $R_{28}$ are each independently of the other hydrogen or $C_1$–$C_4$alkyl, $R_{29}$ is hydrogen, $R_{30}$ is hydrogen, phenyl, $C_1$–$C_{18}$alkyl; $C_2$–$C_{18}$alkyl interrupted by oxygen or by sulfur; $C_7$–$C_9$-phenylalkyl; or $C_7$–$C_{18}$phenylalkyl interrupted by oxygen or by sulfur and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{18}$alkanoyl; $C_3$–$C_{12}$alkanoyl interrupted by oxygen or by sulfur; $C_2$–$C_{12}$-alkanoyl substituted by a di($C_1$–$C_6$alkyl) phosphonate group; $C_6$–$C_9$cycloalkylcarbonyl, benzoyl,

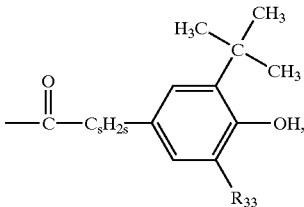

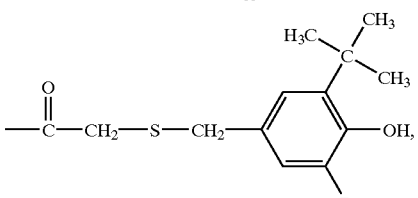

$R_{33}$ is hydrogen or $C_1$–$C_4$alkyl, $R_{34}$ is $C_1$–$C_{12}$alkylene, $C_2$–$C_8$alkylidene, $C_7$–$C_{12}$phenylalkylidene, $C_5$–$C_8$cycloalkylene or phenylene, $R_{35}$ is hydroxy,

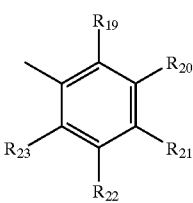

or $C_1$–$C_{18}$alkoxy, $R_{36}$ is oxygen or —NH—, $R_{37}$ is $C_1$–$C_8$alkyl or phenyl, and s is 1 or 2.

4. A process according to claim 1, wherein, when n is 1, $R_1$ is phenanthryl, thienyl, dibenzofuryl, unsubstituted or $C_1$–$C_4$alkyl-substituted carbazolyl; or fluorenyl, or $R_1$ is a radical of formula II

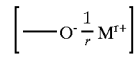

(II)

wherein $R_{19}$, $R_{20}$, $R_{21}$, $R_{22}$ and $R_{23}$ are each independently of the others hydrogen, fluorine, hydroxy, $C_1$–$C_{18}$alkyl, $C_1$–$C_{18}$alkoxy, $C_1$–$C_{18}$alkylthio, phenyl, benzoyl, benzoyloxy or

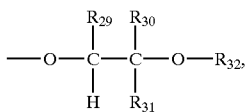

$R_{29}$ is hydrogen, $R_{30}$ is hydrogen, phenyl or $C_1$–$C_{18}$alkyl, $R_{31}$ is hydrogen or $C_1$–$C_4$alkyl, and $R_{32}$ is hydrogen, $C_1$–$C_{12}$alkanoyl or benzoyl.

5. A process according to claim 4, wherein $R_{19}$ is hydrogen or $C_1$–$C_4$alkyl, $R_{20}$ is hydrogen or $C_1$–$C_4$alkyl, $R_{21}$ is hydrogen, fluorine, hydroxy, $C_1$–$C_{12}$alkyl, $C_1$–$C_4$alkoxy, $C_1$–$C_4$alkylthio, phenyl or —O—CH$_2$—CH$_2$—O—R$_{32}$, $R_{22}$ is hydrogen or $C_1$–$C_4$alkyl, $R_{23}$ is hydrogen or $C_1$–$C_4$alkyl, and $R_{32}$ is $C_1$–$C_4$alkanoyl.

6. A process according to claim 1, wherein $R_2$, $R_3$, $R_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; $C_1$–$C_{12}$alkoxy, $C_1$–$C_{12}$alkylthio, $C_1$–$C_4$alkylamino, di($C_1$–$C_4$alkyl)amino, $C_1$–$C_{18}$alkanoyloxy, $C_1$–$C_{18}$alkanoylamino; $C_3$–$C_{18}$alkanoyloxy interrupted by oxygen, sulfur or by

$C_6$–$C_9$cycloalkylcarbonyloxy, benzoyloxy or $C_1$–$C_8$alkyl-substituted benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —(CH$_2$)$_p$—COR$_9$ or —(CH$_2$)$_q$OH or, when $R_3$ and $R_5$ are hydrogen, $R_4$ is additionally a radical of formula IV (IV)

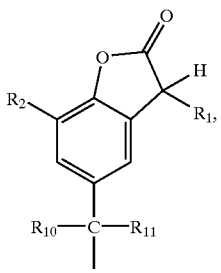

$R_8$ is $C_1$–$C_6$alkyl,

$R_{10}$ and $R_{11}$ are methyl groups or, together with the carbon atom to which they are bonded, form a $C_5$–$C_8$cycloalkylidene ring unsubstituted or substituted by from 1 to 3 $C_1$–$C_4$alkyl groups;

$R_{12}$ and $R_{13}$ are each independently of the other hydrogen or $C_1$–$C_8$alkyl, and q is 2, 3, 4, 5 or 6.

7. A process according to claim 1, wherein at least two of the radicals $R_2$, $R_3$, $R_4$ and $R_5$ are hydrogen.

8. A process according to claim 1, wherein $R_3$ and $R_5$ are hydrogen.

9. A process according to claim 1, wherein $R_2$, $R_3$, $R_4$ and $R_5$ are each independently of the others hydrogen, fluorine, hydroxy, $C_1$–$C_{18}$alkyl, $C_7$–$C_9$phenylalkyl, phenyl, $C_5$–$C_8$cycloalkyl, $C_1$–$C_6$alkoxy, cyclohexylcarbonyloxy or benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —(CH$_2$)$_p$—COR$_9$, or, when $R_3$ and $R_5$ are hydrogen, $R_4$ is additionally a radical of formula IV, $R_9$ is hydroxy or $C_1$–$C_{18}$alkoxy, and $R_{10}$ and $R_{11}$ are methyl groups or, together with the carbon atom to which they are bonded, form a $C_5$–$C_8$cycloalkylidene ring.

10. A process according to claim 1, wherein $R_2$ is $C_1$–$C_{18}$alkyl or cyclohexyl, $R_3$ is hydrogen, $R_4$ is $C_1$–$C_4$alkyl, cyclohexyl, —(CH$_2$)$_p$—COR$_9$ or a radical of formula IV, $R_5$ is hydrogen, $R_9$ is $C_1$–$C_4$alkyl, $R_{10}$ and $R_{11}$, together with the carbon atom to which they are bonded, form a cyclohexylidene ring, and p is 2.

11. A process according to claim 1, wherein $R_2$ is $C_1$–$C_{18}$alkyl or cyclohexyl, $R_3$ is hydrogen, $R'_4$ is $C_1$–$C_4$alkyl, cyclohexyl, —(CH$_2$)$_p$—COR$_9$ or a radical of formula VI, $R_5$ is hydrogen, $R_9$ is $C_1$–$C_4$alkyl, $R_{10}$ and $R_{11}$, together with the carbon atom to which they are bonded, form a cyclohexylidene ring, and p is 2.

12. A process according to claim 1, wherein the catalyst is a metal catalyst.

13. A process according to claim 12, wherein the metal catalyst is a metal catalyst that forms a complex with carbon monoxide.

14. A process according to claim 12, wherein the metal catalyst is a transition metal catalyst.

15. A process according to claim 14, wherein the transition metal catalyst is a titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum or copper catalyst.

16. A process according to claim 14, wherein the transition metal catalyst is a titanium, vanadium, chromium, manganese, iron, ruthenium, cobalt, rhodium, nickel or palladium catalyst.

17. A process according to claim 1, wherein the ratio of molar quantities of the compound of formula V to carbon monoxide is from 1:1 to 1:5000.

* * * * *